(12) United States Patent
Jo et al.

(10) Patent No.: US 6,964,785 B2
(45) Date of Patent: Nov. 15, 2005

(54) HERBAL COMPOSITION FOR IMPROVING ANTICANCER ACTIVITY, IMMUNE RESPONSE AND HEMATOPOIESIS OF THE BODY, AND PROTECTING THE BODY FROM OXIDATIVE DAMAGE, AND THE METHOD OF PREPARING THE SAME

(75) Inventors: Sung Kee Jo, Daejeon (KR); Sung Ho Kim, Gwangju (KR); Sung Tae Yee, Suncheon-si (KR); Hae Ran Park, Daejeon (KR); Heon Oh, Gwangju (KR); Myung Woo Byun, Daejeon (KR)

(73) Assignee: Korea Atomic Energy Research Institute, Daejeon (KR)

(*) Notice: Subject to any disclaimer, the term of this patent is extended or adjusted under 35 U.S.C. 154(b) by 52 days.

(21) Appl. No.: 10/648,416

(22) Filed: Aug. 25, 2003

(65) Prior Publication Data
US 2004/0197427 A1 Oct. 7, 2004

(30) Foreign Application Priority Data
Apr. 7, 2003 (KR) ................................ 10-2003-0021746

(51) Int. Cl.$^7$ ........................ A61K 35/78; A61K 31/715
(52) U.S. Cl. ...................................... 424/725; 424/773
(58) Field of Search ................................ 424/773, 725; 514/54, 885

(56) References Cited

U.S. PATENT DOCUMENTS 4,618,495 A * 10/1986 Okuda et al. ................ 424/728

FOREIGN PATENT DOCUMENTS

| KR | 10-2000-0023772 | 5/2000 |
|---|---|---|
| KR | 2001-100551 | 11/2001 |
| KR | 2002049247 | * 6/2002 |
| KR | 2003043526 | * 6/2003 |
| KR | 2003047212 | * 6/2003 |

OTHER PUBLICATIONS

An article entitled, "Mitrogenic and Complement Activating Activities of the . . . ", By Yamada et al., published by Planta Medica, 58(2), 166–70 CODEN: PLEAA; ISSN: 0032–0943, 1992.

Database WPI, Section Ch, Week 200231, Derwent Publications LTD., London, GB; An 2002–265118 XP002288880 & KR 100 551 A (Korea Atomic Energy Res. Inst.) Nov. 14.

* cited by examiner

Primary Examiner—Christopher R. Tate
(74) Attorney, Agent, or Firm—Bachman & LaPointe, P.C.

(57) ABSTRACT

Disclosed is a herbal composition comprising a first hot-water extract from a mixture of the plants *Angelicae gigantis* Radix, *Cnidium officinale* Makino and *Paeonia japonica* Miyabe et Takeda at an equal weight ratio, and a polysaccharide fraction as a precipitate formed by adding ethanol to a second hot-water extract from a mixture of the plants *Angelicae gigantis* Radix, *Cnidium officinale* Makino and *Paeonia japonica* Miyabe et Takeda at an equal weight ratio. The herbal composition of the present invention is effective in improving the anticancer activity, immune response and hematopoiesis of the body, and protecting the body from oxidative damage. Therefore, by stimulating the recovery from the damage to the immune function and hematopoietic function, often occurring during chemotherapy and radiotherapy, and inhibiting oxidative damage, the herbal composition can be applied for the prevention of the side effects of cancer therapy, as well as for the prevention of various degenerative chronic diseases and the improvement of the health of the weak and the elderly.

10 Claims, 29 Drawing Sheets

HERBAL COMPOSITION FOR IMPROVING ANTICANCER ACTIVITY, IMMUNE RESPONSE AND HEMATOPOIESIS OF THE BODY, AND PROTECTING THE BODY FROM OXIDATIVE DAMAGE, AND THE METHOD OF PREPARING THE SAME

BACKGROUND OF THE INVENTION

1. Field of the Invention

The present invention relates to a herbal composition for improving anticancer activity, immune response and hematopoiesis of the body, and protecting the body from oxidative damage. More particularly, the present invention relates to a herbal composition comprising a first hot-water extract from a mixture of the medicinal plants *Angelicae gigantis* Radix, *Cnidium officinale* Makino and *Paeonia japonica* Miyabe et Takeda at an equal weight ratio, and a polysaccharide fraction as a precipitate formed by adding ethanol to a second hot-water extract from a mixture of the plants *Angelicae gigantis* Radix, *Cnidium officinale* Makino and *Paeonia japonica* Miyabe et Takeda at an equal weight ratio.

2. Description of the Prior Art

Cancer has been treated by directly killing cancer cells by chemotherapy with anticancer agents and radiotherapy, by surgical removal or by activating the immune system participating in the inhibition of cancer cells. In the past, the direct-killing method or surgery were mainly used in cancer therapy. Recently, cancer has been treated by immunotherapy in combination with the direct-killing method. Moreover, with advances in the understanding of the mechanisms of the immune system, much effort has been directed to the employment of immunomodulators for cancer treatment. Immunomodulators enhance the body's immunity by non-specifically stimulating the immune cells, resulting in enhanced protection against disease-causing factors. Examples of the non-specific immunomodulators include inactivated bacterial preparations, chemically synthesized compounds (synthesized nucleic acid derivatives or glycosides), and biological factors (cytokines or hormones). Studies of cancer therapies based on improving the body's immunity using the immunomodulators are in progress. However, owing to their toxicity or side effects, most of the non-specific immunomodulators are limited in their clinical applications. In particular, with the identification of cytokines participating in the immune system, active studies on the use of cytokines in cancer therapy are underway, in which cytokines are produced on a large scale by genetic engineering tools. For example, immunostimulators including interleukin-2 and tumor necrosis factor (TNF) were evaluated for their potential to be applied to cancer therapy, but were demonstrated to have severe side effects and thus have been tried within limited cases.

Hematopoiesis is the process of producing a variety of blood cells including the immune cells from the hematopoietic stem cells of bone marrow, and is closely related to the activity of the immune system. In particular, cytokines acting at each step of the differentiation of the hematopoietic stem cells into the blood cells have been recently identified, and factors inducing proliferation of the hematopoietic cells, such as the granulocyte colony-stimulating factor (G-CSF), have been actively studied to apply them to the treatment of diseases. However, to obtain therapeutic effects, they should be administered to the body in a large quantity. Moreover, in this case, severe side effects are often exhibited, thus limiting their applications.

Cancer treatment by chemotherapy or radiotherapy is accompanied by damage to the hematopoietic system and self-renewal tissues. Such side effects originate from oxidative damage to the tissues by anticancer drugs or radiation. Many efforts have been made to find substances capable of protecting the body from radiation. After the first report in 1949 that cysteine, having a thiol group, has an effect of protecting the body from radiation, research has been focused on aminothiol derivatives (particularly, WR series compounds synthesized by Walter Reed Army Hospital in Washington, D.C.). However, the aminothiol radioprotectors are limited in their clinical application owing to their toxicity. Subsequently, the radioprotective effect of chemically synthesized compounds was studied, including dipyridamole, adenosine monophosphate and deoxyspergualin, but they were also limited in practical applications owing to their severe toxicity. Other efforts to obtain radioprotective effects were made by stimulating the immune and hematopoietic systems using polysaccharides such as glucan and inactivated bacterial preparations such as the streptococcal agent OK-432. Recently, factors associated with the immune responses and hematopoietic functions, which are exemplified by immunostimulators including interleukin-1, the tumor necrosis factor (TNF), hematopoietic cell proliferation-inducing agents such as the granulocyte colony-stimulating factor (G-CSF), and hormones, have been used in studies to obtain the radioprotective effect, but, owing to their side effects, such attempts have been carried out in very limited cases.

As described above, there is an urgent need for the development of substances capable of improving the anticancer function, immune function and hematopoietic function by activating the immune system, as well as protecting the body from the side effects caused by cancer therapy such as radiotherapy. In this regard, a large number of recent studies have focused on the development of physiologically active substances having mild side effects using natural products. In particular, based on the fact that various diseases including aging and cancer are caused by oxidative damage to the body by radiation or chemical compounds as well as by harmful active oxygen species or free radicals, anti-oxidant agents have been studied for their preventive and therapeutic effects against diseases. In addition, efforts to discover physiologically active substances from natural products having the effects of regulating and protecting the body have been actively performed, and some of the discovered natural substances have been applied to food supplements for improving health or as therapeutic agents.

Research aimed at discovering immunomodulators from natural products has focused on the evaluation of the effects of natural plant components or known Chinese herbal materials, and some of the natural substances identified to have immunomodulating activity have been put to practical use. A research group in France reported that the plant *Eleutherococcus senticosus* has an effect of improving recovery from hematopoietic disorder caused by radiation. Also, ginseng, natural pigments, the plant *Codonopsis pilosula*, the plant *Cnidium officinale* Makino, the fungus *Ganoderma lucidum*, and other Chinese herbs and herbal components have been studied for their radioprotective activity, mainly in Japan, Taiwan and China.

Radiation causes disorders of the immune system and the hematopoietic system, as well as damage to the self-renewal tissues. Based on the results of researches for Chinese herbal materials with a protective effect against each symptom accompanying radiation treatment, the present inventors previously tried to find a herb combination capable of overcoming all of the symptoms following radiation treatment, resulting in the finding that a herbal composition, prepared by mixing the plants *Angelicae gigantis* Radix, *Cnidium officinale* Makino and *Paeonia japonica* Miyabe et Takeda at an equal weight ratio, and extracting the mixture by hot water, was safer than the conventional immunostimulating drugs. The herbal composition is disclosed in Korean Pat. Application No. 2000-23772. However, with respect to increasing the body's immune function and the hematopoietic function, the herbal composition has just 2–3-fold higher effects when compared to a control with no administration of the herbal composition, and limited effects on activation of the anticancer immune responses.

SUMMARY OF THE INVENTION

It is therefore an object of the present invention to provide a herbal composition having the effects of improving the anticancer activity, immune response and hematopoiesis of the body, where the effect is higher than the conventional drugs having the effects of enhancing the immune and hematopoietic functions, as well as being capable of protecting the body from oxidative damage, using the medicinal plants *Angelicae gigantis* Radix, *Cnidium officinale* Makino and *Paeonia japonica* Miyabe et Takeda.

It is another object of the present invention to provide a pharmaceutical composition comprising such a herbal composition as an effective ingredient.

It is a further object of the present invention to provide a functional food comprising such a herbal composition as an effective ingredient.

BRIEF DESCRIPTION OF THE DRAWINGS

The above and other objectives, features and other advantages of the present invention will be more clearly understood from the following detailed description taken in conjunction with the accompanying drawings, in which.

DETAILED DESCRIPTION OF THE INVENTION

Figure 1:
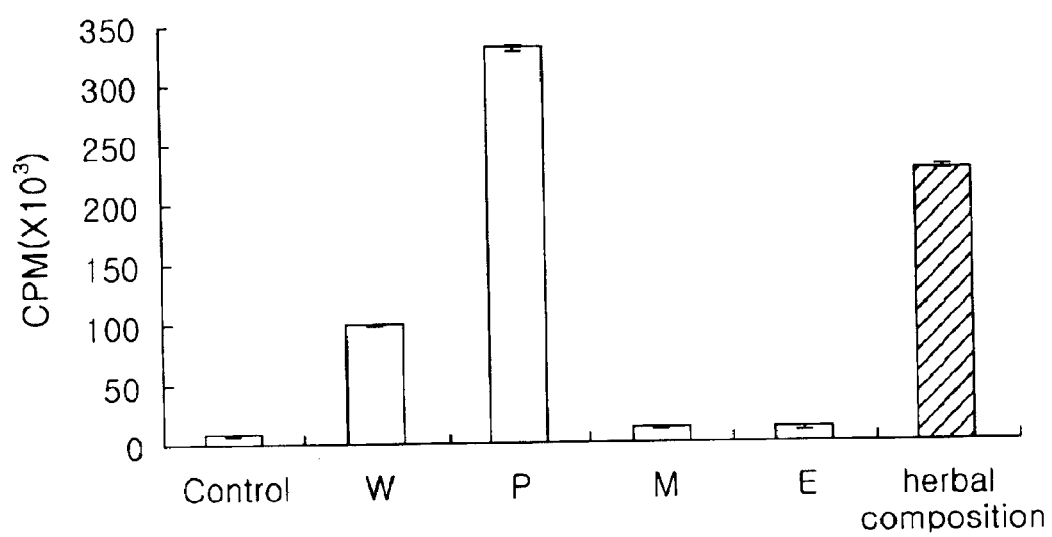
FIG. 1 is a graph showing the immune cell-activating effects of the fractions of a hot-water extract and a herbal composition of the present invention (C: control, W: hot-water extract, P: polysaccharide fraction, M: methanol-soluble fraction, and E: ethanol-soluble fraction)

To achieve the objectives as described above, the present invention provides a herbal composition comprising a first hot-water extract from a mixture of the medicinal plants *Angelicae gigantis* Radix, *Cnidium officinale* Makino and *Paeonia japonica* Miyabe et Takeda at an equal weight ratio, and a polysaccharide fraction as a precipitate formed by adding ethanol to a second hot-water extract from a mixture of the plants *Angelicae gigantis* Radix, *Cnidium officinale* Makino and *Paeonia japonica* Miyabe et Takeda at an equal weight ratio.

Also, the present invention provides a pharmaceutical composition for treating cancer, improving the immune function and hematopoietic function of the body, protecting the body from oxidative damage, and preventing the side effects of cancer therapy, which comprises such a herbal composition as an effective ingredient.

The present invention further provides a functional food comprising such a herbal composition.

The present invention still further provides a method of preparing a herbal composition, comprising the following steps: (1) preparing the mixture consisting of the plants *Angelicae gigantis* Radix, *Cnidium officinale* Makino and *Paeonia japonica* Miyabe et Takeda at an equal weight ratio, adding water at 5 to 20 times the total weight of the mixture, and heating the resulting mixture to prepare a first hot-water extract; (2) adding ethanol to a second hot-water extract prepared according to the same method as Step (1), and collecting a precipitate to obtain a polysaccharide fraction; and (3) mixing the polysaccharide fraction prepared at Step (2) with the hot-water extract prepared at Step (1) to generate a herbal composition.

The present inventors believed that the hot-water extract from a mixture consisting of an equal weight ratio of the plants *A. gigantis, C. officinale* and *P. japonica* contains ingredients especially effective in improving the anticancer function, immune function and hematopoietic function of the body, and in protecting the body from oxidative damage, and that the identification of such ingredients can lead to the development of a herbal composition having a better anticancer activity than the conventional anticancer compositions.

In this regard, the hot-water extract from a mixture consisting of an equal weight ratio of the plants *A. gigantis, C. officinale* and *P. japonica* was separated into a methanol fraction, an ethanol fraction, and a polysaccharide fraction that is the precipitate formed by ethanol addition. Various tests resulted in the finding that the polysaccharide fraction has an excellent effect on the improvement of the anticancer function, immune function and hematopoietic function of the body. With respect to the protection from oxidative damage, the polysaccharide fraction was found to be slightly less effective than the methanol fraction and the ethanol fraction.

Based on these findings, the present inventors identified that, when the hot-water extract from a mixture consisting of an equal weight ratio of the plants *A. gigantis, C. officinale* and *P. japonica* is used in combination with the polysaccharide fraction that is a precipitate formed by adding ethanol to the hot-water extract to increase the content of polysaccharide, the resulting mixture, referred to as "herbal composition" herein, has an improved effect of protecting the body from oxidative damage, and improving the hematopoietic function, anticancer function and immune function.

In the following, the effects of the hot-water extract from the mixture of the plants *A. gigantis, C. officinale* and *P. japonica* at an equal weight ratio, and its three fractions, i.e. methanol-soluble, ethanol-soluble, and polysaccharide fractions, will be shown and compared in figures regarding each parameter as described above, so it can be shown that the combined composition prepared by adding the polysaccharide fraction to the hot-water extract, thus increasing the content of the polysaccharide, has improved effects. Next, the effects of the herbal composition prepared by combining the hot-water extract with the polysaccharide fraction will be described in more detail in conjunction with examples.

Effects of Fractions Isolated from the Hot-Water Extract from the Herb Mixture (1) Isolation of Fractions from the Hot-Water Extract from the Herb Mixture The three plants *A. gigantis, C. officinale* and *P. japonica*, which are registered as food materials in the Korean Food Code and used as Chinese herbal materials, were dried in the shade, cut and mixed at an equal weight ratio. The plant mixture was added with 10 weight equivalents of distilled water, and boiled for 8–10 hrs in a vessel for extracting Chinese medicinal herbs, thus giving a hot-water extract (hot-water extract: W fraction). Methanol was added to the hot-water extract to obtain a methanol-soluble fraction (M fraction). Ethanol was added to the hot-water extract to obtain an ethanol-soluble fraction (E fraction). Also, when ethanol was added to the hot-water extract at a final concentration of 80%, followed by incubation at 5–15° C. overnight, a precipitate was obtained, resulting in the production of a polysaccharide fraction (P fraction).

(2) Evaluation of the Effects of the Isolated Fractions

Each fraction of the hot-water extract was evaluated for the effects of activating the immune cells, enhancing the hematopoietic function, and reducing oxidative damage in the body.

First, the activation of the immune cells was investigated as follows.

If the splenic immune cells are activated when cultured in a culture medium supplemented with each fraction of the hot-water extract, the immune cells proliferate with increased cellular metabolism and cell division involving DNA replication. Therefore, activation of the splenic immune cells can be analyzed by adding a radioactive DNA precursor ($^3$H-labeled thymidine) to the culture medium, and measuring the amount of the isotope incorporated in the immune cells. Such a $^3$H-thymidine uptake assay was performed as follows.

The immune cells (lymphocytes) collected from mouse spleens were suspended in a complete medium and aliquotted onto a 96-well flat-bottomed microplate at a density of $2 \times 10^5$ cells/ml, and treated with each fraction of the hot-water extract. After incubation for 3 days in a $CO_2$ incubator, $^3$H-thymidine was added to the culture-well at an amount of 1.5 $\mu$Ci per well. After incubation for 4 more hrs, cells were harvested on a glass-fiber filter paper using a cell harvester. The paper strip was put into a counting vial and 3 ml of a scintillation cocktail was added to the vial. $^3$H-thymidine incorporated in the cells was measured in a $\beta$-scintillation counter, and the results were expressed as the arithmetic mean of the counts per minute (cpm).

As shown in FIG. 1, it was found that the polysaccharide fraction significantly activated the splenic immune cells, and such an activation was 3-fold higher than that of the hot-water extract. In contrast, the methanol-soluble fraction and the ethanol-soluble fraction were barely effective in activating the immune cells.

Next, the effect of the hot-water extract and its isolated fractions on the hematopoietic function was investigated as follows.

Primarily, the hot-water extract and its fractions were evaluated for their effect on the proliferation of the bone marrow stem cell.

The bone marrow stem cells, which are non-adherent cells obtained from bone marrow cells, differentiate into monocytes/macrophages, platelets, erythrocytes, etc. After culturing bone marrow cells in a culture medium supplemented with each fraction of the hot-water extract, the non-adherent cells were collected along with the culture supernatant. Proliferation of the bone marrow stem cells was investigated by measuring the cell numbers using a cell counter. The results are given in FIG. 2a.

Figure 2A:
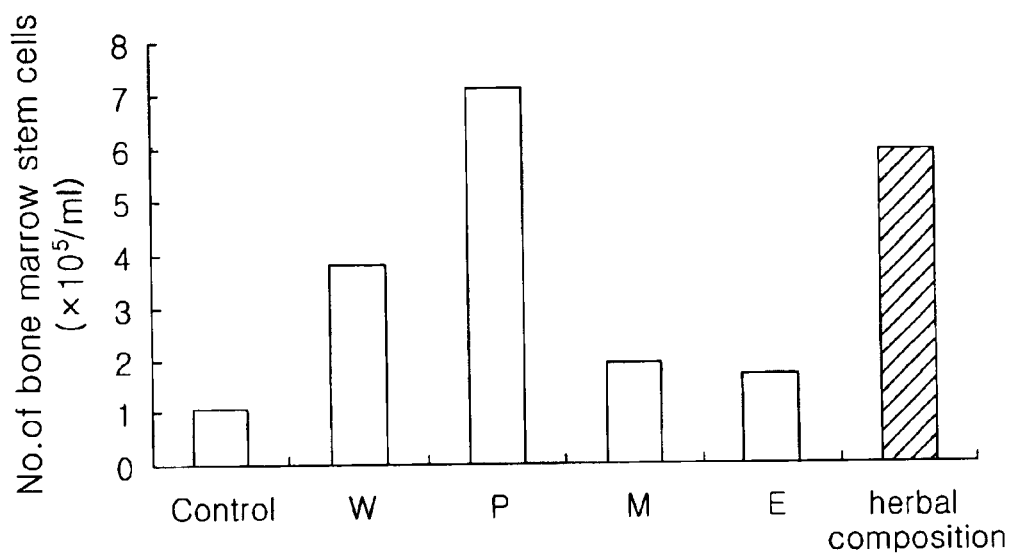
FIG. 2a is a graph showing the hematopoietic function-improving effects of the fractions of a hot-water extract and the herbal composition of the present invention by stimulating the proliferation of the bone marrow stem cells.

As shown in FIG. 2a, it was found that the polysaccharide fraction of the hot-water extract significantly stimulates the proliferation of the bone marrow stem cells, and such a stimulation effect was about 2-fold higher than that of the hot-water extract. On the other hand, the methanol fraction and the ethanol fraction were found to have a much weaker stimulation effect than the hot-water extract.

Then, the hot-water extract and its fractions were evaluated for their effect on the proliferation of the bone marrow stromal cells.

It has been reported that a variety of hematopoietic factors (proteinacious factors, cytokines, etc.) secreted from the stromal cells participate in the proliferation of the bone marrow stem cells and their differentiation into diverse mature cells, and the contact of the bone marrow stem cells with the stromal cells near them is critical for such proliferation and differentiation. Therefore, it is believed that the stromal cells in the hematopoietic microenvironment play an important role in regulating hematopoiesis.

Figure 2B:
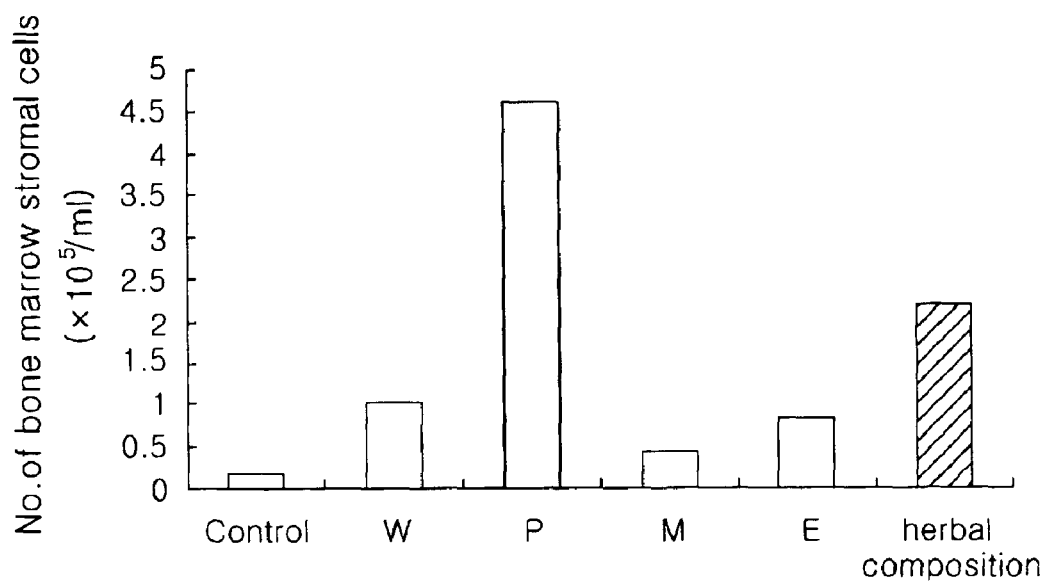
FIG. 2b is a graph showing the hematopoietic function-improving effects of the fractions of a hot-water extract and the herbal composition of the present invention by stimulating the proliferation of the bone marrow stromal cells.
Figure 3A:
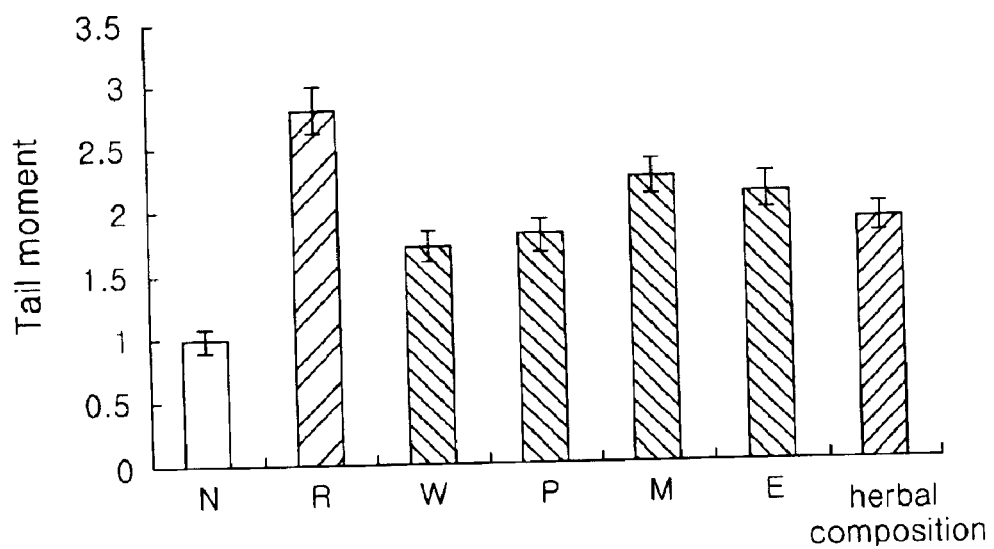
FIG. 3a is a graph showing the inhibitory effects of the fractions of a hot-water extract and the herbal composition of the present invention against DNA oxidative damage induced by radiation (N: normal control, R: radiation-exposed control, W: hot-water extract, P: polysaccharide fraction, M: methanol-soluble fraction, and E: ethanol-soluble fraction)
Figure 3B:
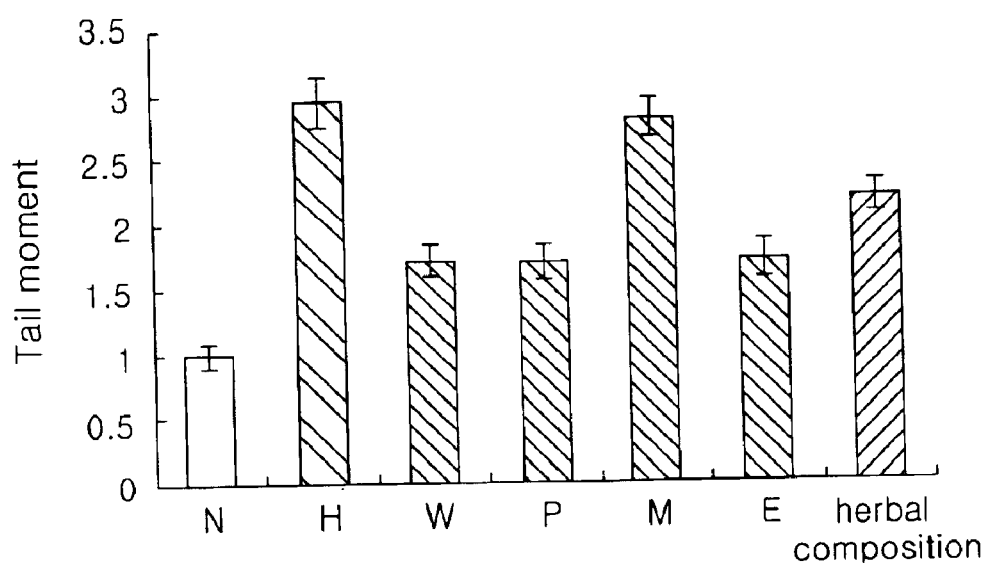
FIG. 3b is a graph showing the inhibitory effects of the fractions of a hot-water extract and the herbal composition of the present invention against DNA oxidative damage induced by hydrogen peroxide (N: normal control, H: $H_2O_2$ treated-control, W: hot-water extract, P: polysaccharide fraction, M: methanol-soluble fraction, and E: ethanol-soluble fraction)
Figure 4A:
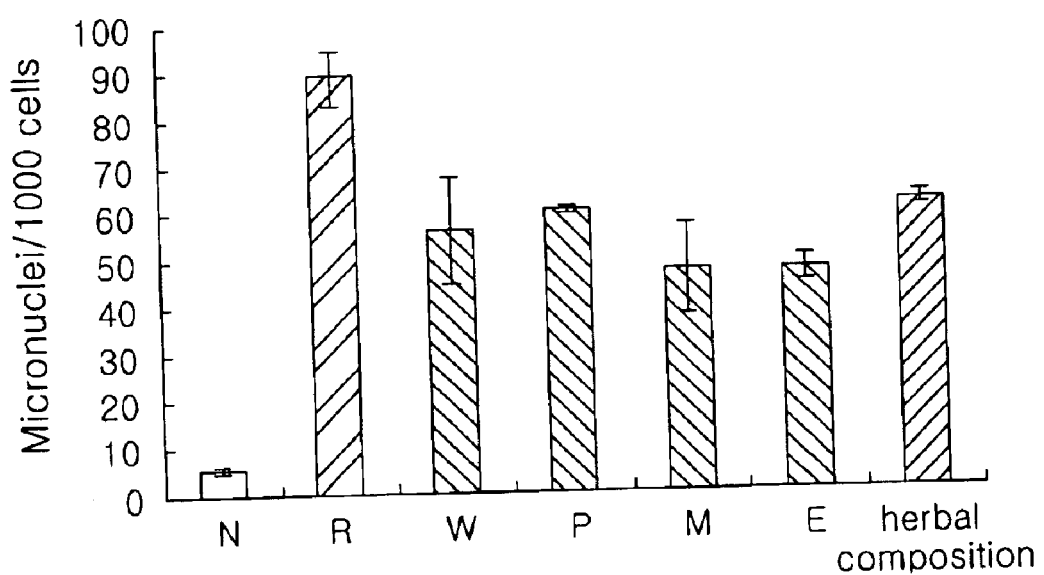
FIG. 4a is a graph showing the inhibitory effects of the fractions of a hot-water extract and the herbal composition of the present invention against chromosome oxidative damage induced by radiation.
Figure 4B:
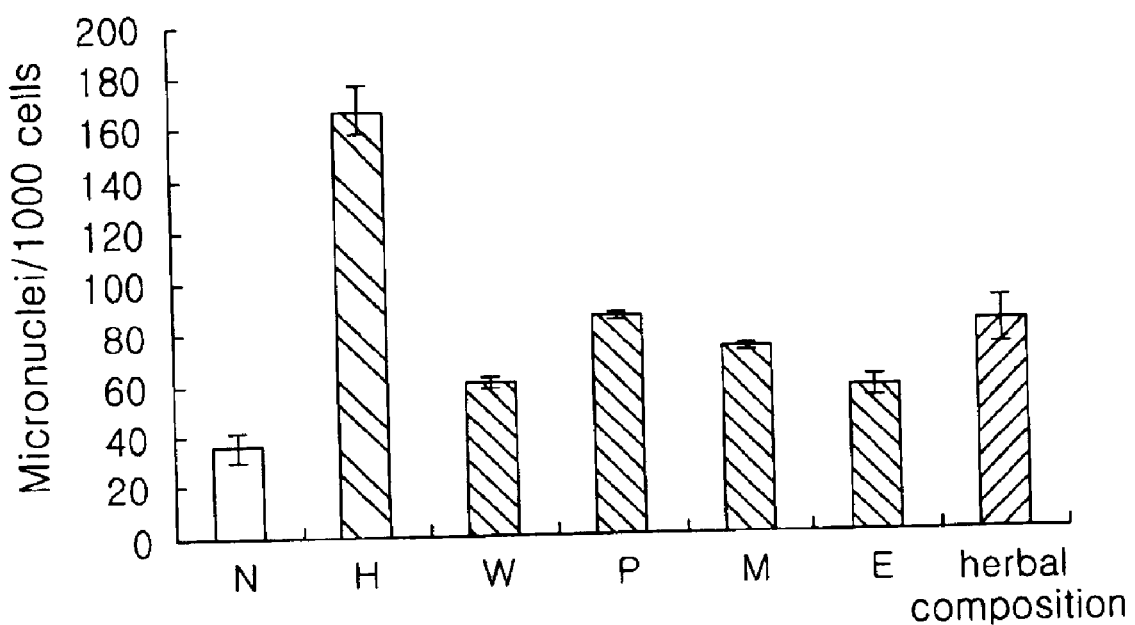
FIG. 4b is a graph showing the inhibitory effects of the fractions of a hot-water extract and the herbal composition of the present invention against chromosome oxidative damage induced by hydrogen peroxide.

Effect of the hot-water extract and its fractions on the proliferation of the bone marrow stromal cells was investigated. Bone marrow cells were cultured to obtain stromal cells adhering to the bottom of the culture dishes. The isolated bone marrow stromal cells were cultured for a long period of time. During the culturing, about half of the cultured medium was exchanged with a fresh medium at intervals of 7 days. The cells were treated with each fraction of the hot-water extract, followed by incubation for 2–3 weeks. Proliferation of the bone marrow stromal cells was analyzed by measuring the cell numbers. The results are given in FIG. 2b. As shown in FIG. 2b, the polysaccharide fraction exhibited a strong stimulating activity toward proliferation of the stromal cells, and such an activity was over 4-fold higher than that of the hot-water extract.

Finally, the hot-water extract and its fractions were evaluated for the reducing effect against oxidative damage in the body.

Cells were treated with each fraction of the hot-water extract, incubated for 4 hrs in a $CO_2$ incubator, and treated with radiation or hydrogen peroxide. DNA damage and chromosome damage were compared with a control, and the results are given in FIGS. 3a, 3b, 4a and 4b. As shown in FIGS. 3a, 3b, 4a and 4b, the polysaccharide fraction was found to have a reducing effect against DNA damage and chromosome damage caused by radiation or hydrogen peroxide, and such a reducing effect was slightly stronger than or similar to the ethanol fraction, the methanol fraction and the hot-water extract.

Figure 5A:
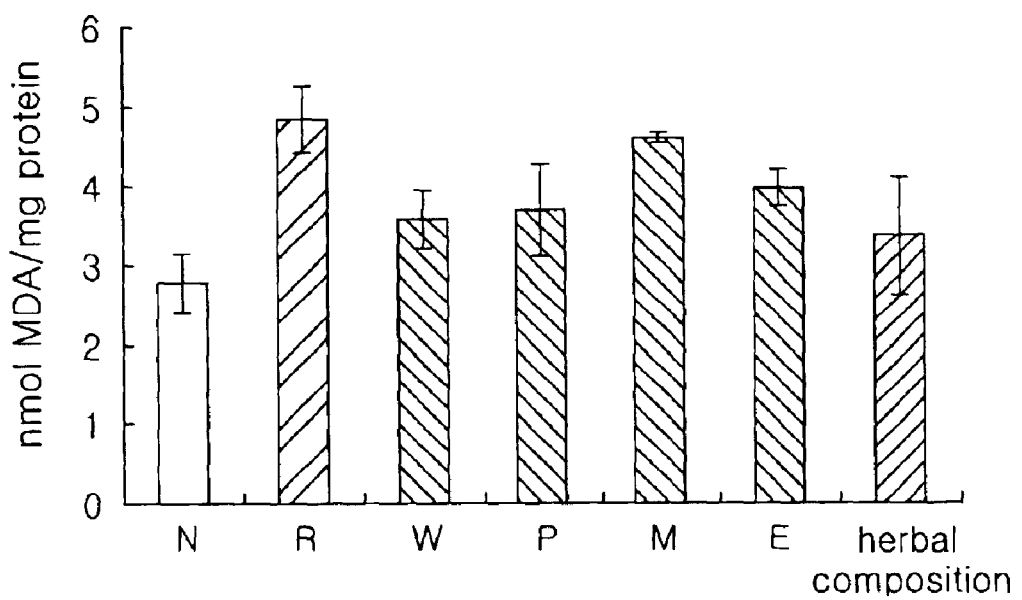
FIG. 5a is a graph showing the inhibitory effects of the fractions of a hot-water extract and the herbal composition of the present invention against lipid oxidative damage induced by radiation.
Figure 5B:
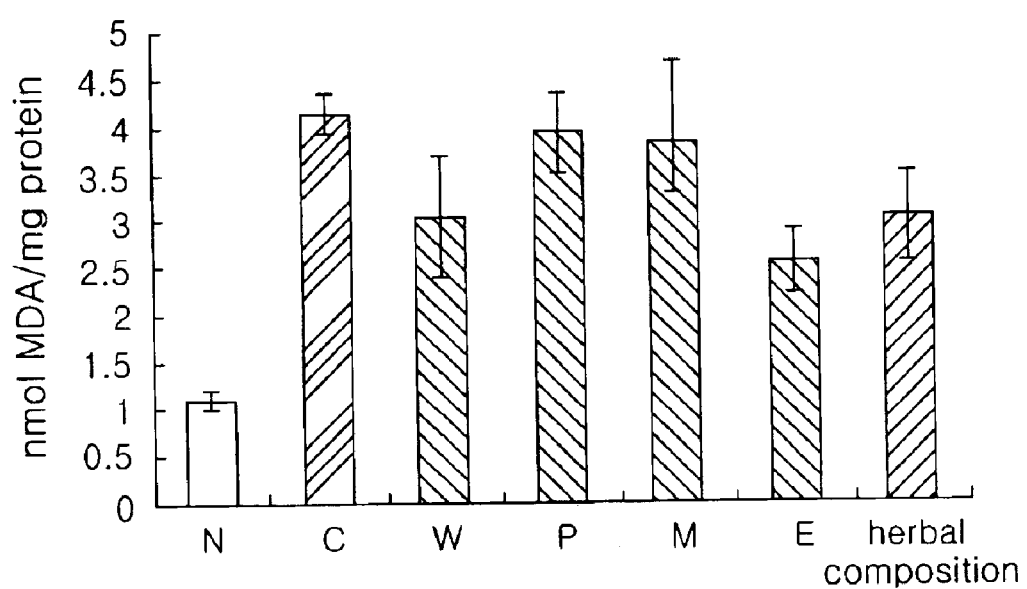
FIG. 5b is a graph showing the inhibitory effects of the fractions of a hot-water extract and the herbal composition of the present invention against lipid oxidative damage induced by $CCl_4$ (N: normal control, C: $CCl_4$ treated-control, W: hot-water extract, P: polysaccharide fraction, M: methanol-soluble fraction, and E: ethanol-soluble fraction)
Figure 5C:
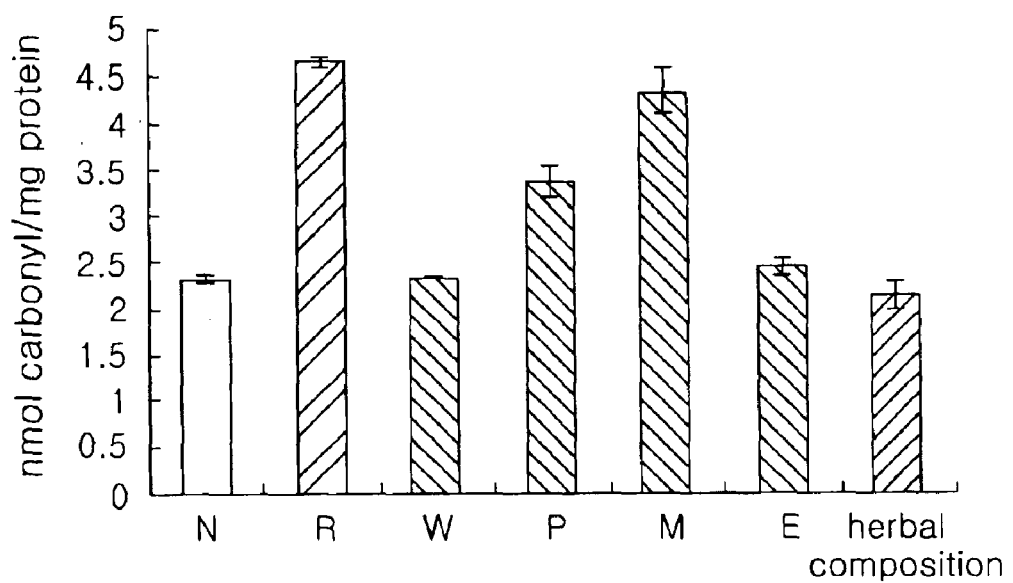
FIG. 5c is a graph showing the inhibitory effects of the fractions of a hot-water extract and the herbal composition of the present invention against protein oxidative damage induced by radiation.

In addition, the inhibitory effect of each fraction of the hot-water extract against peroxidation of the membrane lipids and proteins caused by radiation and oxidative damage is shown in FIGS. 5a to 5c. As shown in FIGS. 5a to 5c, the polysaccharide fraction has a slightly weaker inhibitory effect against peroxidation of the membrane lipids and proteins than the ethanol fraction and the hot-water extract.

Figure 6A:
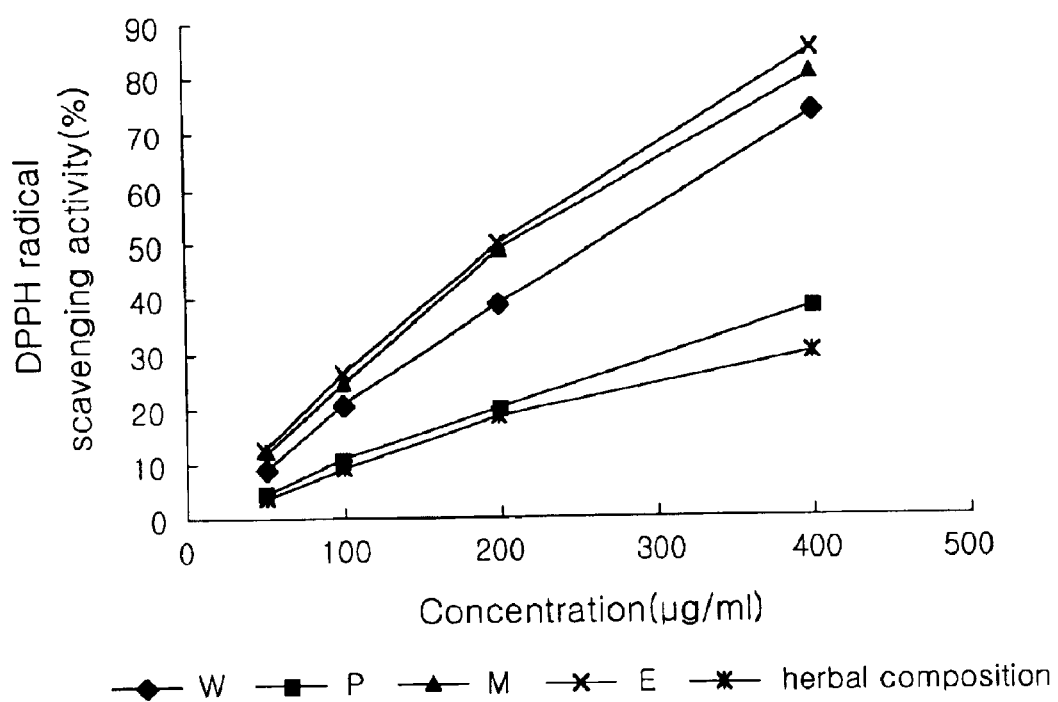
FIG. 6a is a graph showing the DPPH radical-scavenging effect of the fractions of a hot-water extract and the herbal composition of the present invention.
Figure 6B:
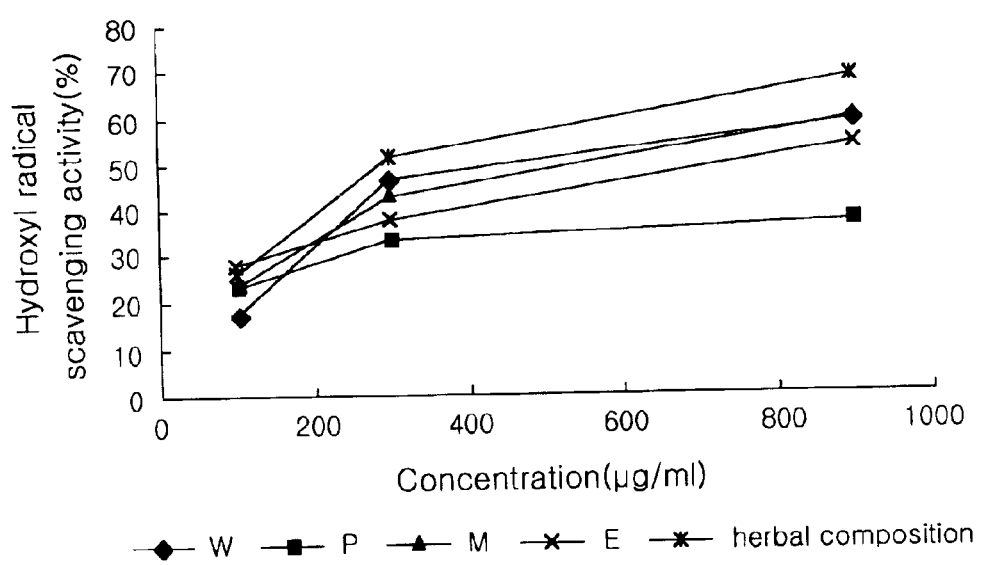
FIG. 6b is a graph showing the OH radical-scavenging effect of the fractions of a hot-water extract and the herbal composition of the present invention.

Further, the reducing effect of each fraction of the hot-water extract against oxidative damage by the scavenging free radicals generated in the body is shown in FIGS. 6a and 6b. As shown in FIGS. 6a and 6b, the polysaccharide fraction has a weaker free radical-scavenging effect than the ethanol-soluble fraction and the methanol-soluble fraction.

As described above, with respect to the effects of improving the anticancer function, immune function and hematopoietic function, the polysaccharide fraction was found to be superior to the ethanol and methanol fractions and the hot-water extract. However, the hot-water extract displayed a slightly higher protective effect against oxidative damage than the polysaccharide fraction. Therefore, when a herbal composition is prepared by combining the hot-water extract with the polysaccharide fraction to increase the content of the polysaccharide, all of the aforementioned advantageous effects can be obtained. The herbal composition having an increased polysaccharide content by combining the hot-water extract with the polysaccharide fraction is described in more detail, as follows.

Herbal Composition According to the Present Invention

The herbal composition of the present invention comprising a first hot-water extract from the mixture of the plants *Angelicae gigantis* Radix, *Cnidium officinale* Makino and *Paeonia japonica* Miyabe et Takeda at an equal weight ratio, and a polysaccharide fraction as a precipitate formed by adding ethanol to a second hot-water extract from the mixture of the plants *Angelicae gigantis* Radix, *Cnidium officinale* Makino and *Paeonia japonica* Miyabe et Takeda at an equal weight ratio.

In detail, the herbal composition of the present invention is prepared by a process comprising the following steps: (1)

preparing the mixture consisting of the plants *Angelicae gigantis* Radix, *Cnidium officinale* Makino and *Paeonia japonica* Miyabe et Takeda at an equal weight ratio, adding water at 5 to 20 times the total weight of the mixture, and heating the resulting mixture to prepare a first hot-water extract; (2) adding ethanol to a second hot-water extract prepared according to the same method as Step (1), and collecting a precipitate to obtain a polysaccharide fraction; and (3) mixing the polysaccharide fraction prepared at Step (2) with the hot-water extract prepared at Step (1) to generate a herbal composition.

The hot-water extraction at Step (1) is preferably performed by boiling the plants for 8–10 hrs in a vessel for extracting Chinese medicinal herbs using hot water. The boiled product may be filtered, and concentrated by an evaporator under a negative pressure. At Step (2), it is preferable that the ethanol is added to the second hot-water extract at a final concentration of 80%, and the second hot-water extract is then incubated at 5–15° C. overnight to obtain a precipitate, that is, the polysaccharide fraction.

To produce a herbal composition, the polysaccharide fraction is mixed up with the first hot-water extract prepared at Step (1), in which the mixture may be used itself, or formulated into powder by freeze-drying.

Preferably, the polysaccharide fraction is contained in the herbal composition at a 1.5 to 4-fold higher concentration than in the first hot-water extract. Therefore, to obtain the polysaccharide fraction within the above range, at Step (2), the second hot-water extract is preferably used at an amount of 0.5 to 3 times that of the first hot-water extract prepared at Step (1).

In accordance with the present invention, a pharmaceutical composition comprising the herbal composition as described above as an effective ingredient is provided. The pharmaceutical composition may be administered orally or parenterally, and used in a pharmaceutical formulation common in the art.

That is, upon being clinically applied, the pharmaceutical composition of the present invention may be administered orally or parenterally in various formulations. The pharmaceutical composition may be formulated into a pharmaceutical preparation using a filler, a thickening agent, a binder, a humectant, a disintegrator, a diluent such as a surfactant, or an excipient. Examples of solid preparations for oral administration include tablets, pills, powder, granules and capsules. Such solid preparations may contain one or more excipients selected from starch, calcium carbonate, sucrose or lactose, and gelatin. In addition to the simple excipient, the solid preparations may also contain a lubricant such as magnesium stearate or talc. Examples of liquid preparations for oral administration include suspensions, liquid solutions such as elixirs, emulsions and syrups. The liquid preparations may contain a simple diluent such as water or liquid paraffin, and various excipients, which are exemplified by humectants, sweetening agents, aromatic agents and preservatives. Examples of pharmaceutical preparations for parenteral administration include sterilized aqueous solutions, non-liquid solutions, suspensions, emulsions, freeze-dried preparations and suppositories. The non-liquid solutions and suspensions may be prepared using propylene glycol, polyethylene glycol, vegetable oils such as olive oil, and injectable esters such as ethyloleate. Bases for the suppositories may include Witepsol, Macrogol, Tween-61, cacao butter, laurin fat and glycerogelatin.

Daily dosage of the pharmaceutical composition of the present invention is 30–300 mg/kg, but preferably, 80–150 mg/kg. The daily dosage may be separately administered over 1–3 times.

In accordance with the present invention, a functional food comprising the herbal composition as described above as an effective ingredient is provided. The functional food may further comprise a food additive according to consumers' preferences and to improve quality of the final food.

The present invention will be explained in more detail with reference to the following example in conjunction with the accompanying drawings. However, the following example is provided only to illustrate the present invention, and the present invention is not limited to the example.

EXAMPLE

Preparation of the Herbal Composition

The three plants *A. gigantis, C. officinale* and *P. japonica*, which are registered as food materials in the Korean Food Code and used as Chinese herbal materials, were dried in the shade, cut and mixed at an equal weight ratio. The plant mixture was added with 10 weight equivalents of distilled water, and boiled for 8–10 hrs in a vessel for extracting Chinese medicinal herbs. The boiled product was filtered and concentrated using an evaporator under a negative pressure, thus yielding a hot-water extract. A fourth to two-thirds of the concentrated solution was stored, and the remainder, a third to three-fourths of the concentrate, was mixed with ethanol at a final concentration of 80%, followed by incubation at 5–15° C. overnight. The resulting precipitate polysaccharide fraction was collected, and mixed with the stored hot-water extract. The mixture can be used itself or in a formulation of powder prepared by freeze-drying. To be used in the following tests, half of the concentrate is stored and ethanol is added to the remaining half of the concentrate. Then, the remaining half added with ethanol is incubated at 5–15° C. overnight and the resulting precipitate polysaccharide fraction was collected, and mixed with the half of the concentrate stored. After freeze-drying this mixture, the resulting herbal powder was properly dissolved in distilled water, and sterilized by filtration via a 0.45 μm membrane (Millipore) and used in the following tests.

In the following experimental example, "control" is the group treated with saline instead of the herbal composition of the present invention, and among this control, the group additionally treated with radiation is referred to as the "radiation control", the group additionally treated with $H_2O_2$ is referred to as the "H-control", the group additionally treated with $CCl_4$ is referred to as the "C-control", and the group treated with no radiation or chemicals is referred to as the "normal control".

Experimental Example 1

Evaluation of the Anticancer Activity of the Herbal Composition and its Effects on the Immune Function 1) Inhibitory Effect Against Tumor Growth To investigate anticancer activity of the filtered herbal composition prepared in the above Example, tumor-injected mice were treated with the herbal composition, in which a saline solution was used as a control. As a result, the herbal composition of the present invention was found to have an effect of inhibiting tumor growth.

Male and female mice (BDF1, 7 weeks old) were intraperitoneally injected with $1 \times 10^5$ B16F0 melanoma cells. From the following day, the herbal composition of the present invention and the control sample were intraperitoneally administered into the mice for 10 days. Thereafter, surviving mice were counted every day, and the results are given in FIGS. 7a and 7b.

Figure 7A:
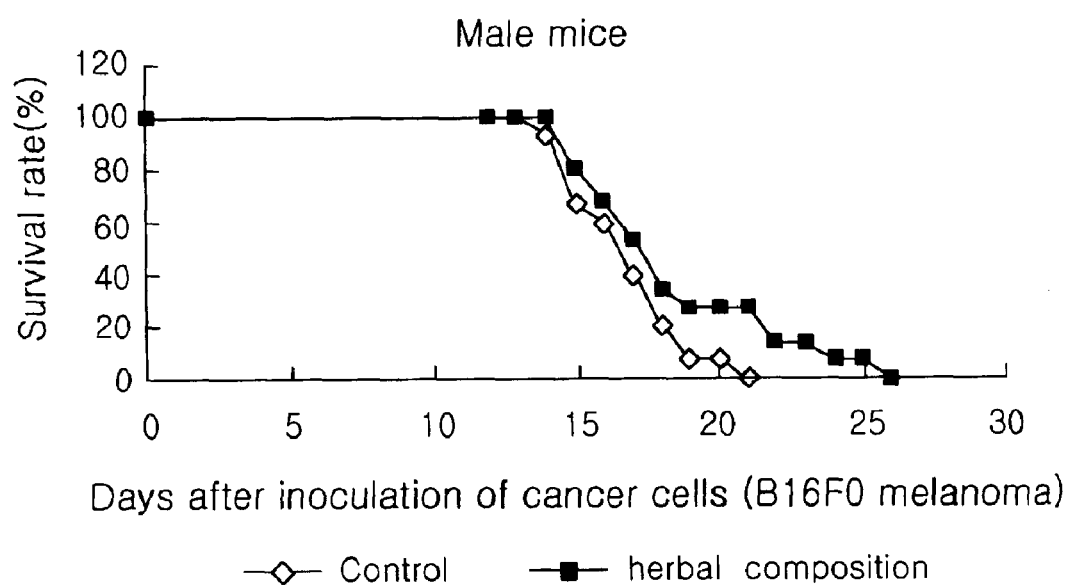
FIG. 7a is a graph showing the inhibitory effect of the herbal composition of the present invention against tumor growth in male mice, resulting in an increase of their life span.
Figure 7B:
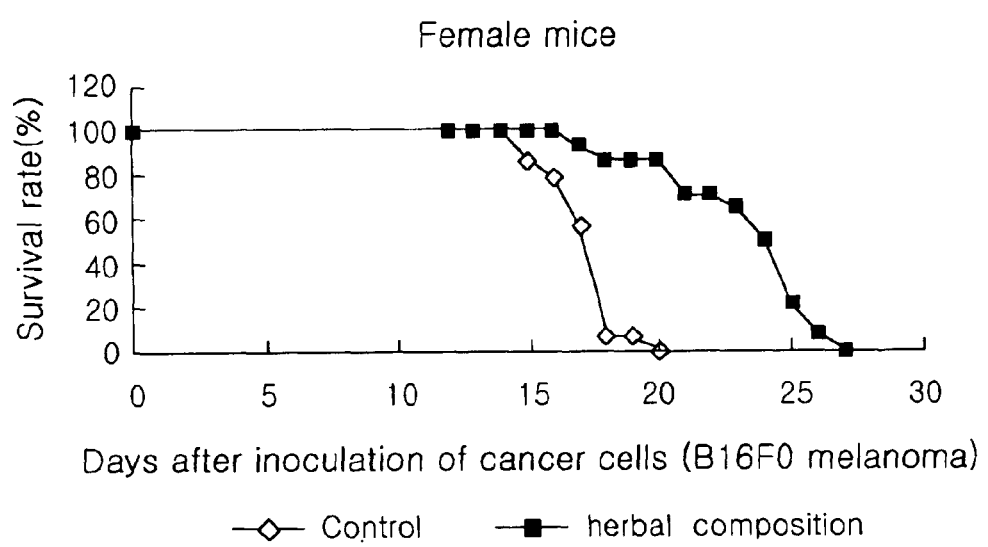
FIG. 7b is a graph showing the inhibitory effect of the herbal composition of the present invention against tumor growth in female mice, resulting in an increase of their life span.

As shown in FIG. 7a, in the case of the tumor-injected male mice, all mice of the control group were dead by day 21, while some mice of the group treated with the herbal composition survived until day 25, in which the survival time of the male mice treated with the herbal composition was prolonged by about 15%. As shown in FIG. 7b, in the case of female mice, the mice of the control group were dead by day 19. In contrast, about 50% of the female mice of the treatment group survived until day 24, and some of them survived until day 26, in which the survival time of the female mice was prolonged by about 34%.

These results indicate that the herbal composition of the present invention exhibits anticancer activity by inhibiting the growth of the tumor cells.

Figure 8:
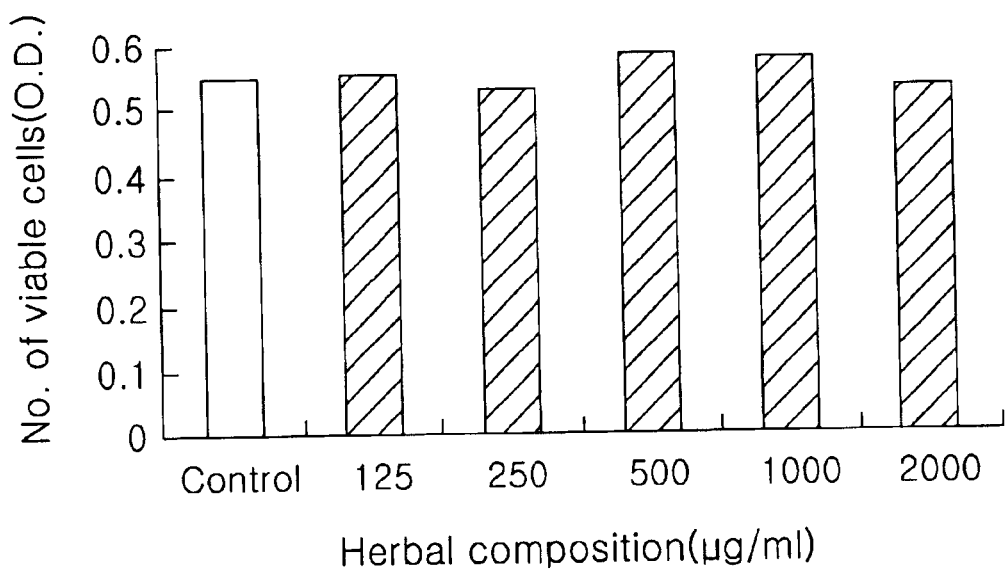
FIG. 8 is a graph showing no effect of the herbal composition of the present invention on the direct killing or growth inhibition of tumor cells in vitro.

On the other hand, to investigate whether the herbal composition exhibits anticancer activity by directly killing tumor cells, tumor cells were treated with the herbal composition of the present invention in a test tube, and their viability was analyzed. That is, B16F0 melanoma cells were suspended in complete medium and aliquotted onto a 96-well flat-bottomed microplate at a density of $5 \times 10^4$ cells per well, and treated with the herbal composition. After incubation for 1 day in a $CO_2$ incubator, a MTT solution was added to the culture-wells, followed by incubation for 4 more hrs. Living cells convert MTT into formazan, and the formazan product is deposited in the living cells. The water-insoluble formazan product deposited in living cells was solubilized by adding 0.07 N HCl in isopropanol to each well, and quantified by measuring the absorbance at 570 nm using a UV spectrometer. The measured absorbance was converted to a relative number of living cells. The results are given in FIG. 8. As shown in FIG. 8, there is no difference in living cell numbers between the groups treated with the herbal composition or not. These results indicate that the herbal composition of the present invention neither directly kills tumor cells nor directly inhibits their proliferation.

2) Effect of Enhancing the Immune Function 2.1) Effect of Activating the Immune Cells If the splenic immune cells are activated when cultured in a culture medium supplemented with the herbal composition and the hot-water extract from a mixture of three plants *A. gigantis*, *C. officinale* and *P. japonica*, which were prepared in the above Example, the immune cells proliferate with increased cellular metabolism and cell division involving DNA replication. Therefore, activation of the splenic immune cells can be analyzed by adding a radioactive DNA precursor ($^3$H-labeled thymidine) to the culture medium, and measuring the amount of isotopes incorporated in the splenocytes. Such a $^3$H-thymidine uptake assay was performed as follows.

The immune cells (lymphocytes) collected from mouse spleens were suspended in complete medium and aliquotted onto a 96-well flat-bottomed microplate at a density of $2 \times 10^5$ cells per well, and treated with the herbal composition and the hot-water extract. After incubation for 3 days in a $CO_2$ incubator, $^3$H-thymidine was added to the medium at an amount of 1.5 $\mu$Ci per well. After incubation for 4 more hrs, cells were harvested on a glass-fiber filter paper using a cell harvester. The paper strip was put into a counting vial and a 3 ml scintillation cocktail was added to the vial. $^3$H-thymidine uptake was measured in a β-scintillation counter, and the results were expressed as the average counts per minute (cpm). The results are given in FIG. 1.

As shown in FIG. 1, the herbal composition was found to be remarkably effective at activating the immune cells, and such an effect was 2 times higher than that of the hot-water extract, and 10 times higher than the control not treated with any herbal extract.

2.2) Effect of Improving the Anticancer Function by Activating the NK Cells

Natural killer (NK) cells, which belong to a primary protection system against tumor cells, eliminate tumor cells in a non-specific manner. In this test, the herbal composition of the present invention was evaluated for its effects on increasing the cytotoxicity of the NK cells against the tumor cells.

Mice were intraperitoneally administered with the herbal composition (1 mg/mouse) once daily for 3 days. Next day, after sacrificing the mice, splenic immune cells were isolated from the spleen, and used as effector cells in the following chromium release assay to analyze their cytolytic activity against the target cells (tumor cells).

$2 \times 10^6$ YAC-1 cells (mouse lymphoma) as target cells were labeled with $Na_2{}^{51}CrO_4$ (40 $\mu$Ci) in a 37° C. water bath for 1 hr. The isolated splenocytes as effector cells (referred as E) and the labeled target cells (referred as T) were aliquotted onto a 96-well microplate at ratios of 50:1 and 100:1. After incubation for 4 hrs, 100 $\mu$l of the culture supernatant was collected into a tube, and was analyzed for the amount of radioactive chromium released from the dead tumor cells in a gamma-counter, and the results were expressed as the average counts per minute (cpm). All tests were carried out in triplicate, and the cytotoxicity of the NK cells against the tumor cells was calculated according to the following Equation 1:

$$\% \text{ Cytotoxicity} = (ER-SR)/(MR-SR) \times 100 \quad \text{(Equation 1)}$$

wherein, ER (experimental release, cpm) is the experimental $^{51}$Cr release from the labeled target cells co-cultured with the effector cells to the culture supernatant, SR (spontaneous release, cpm) is spontaneous $^{51}$Cr release from the labeled target cells incubated alone to the culture supernatant, and MR (maximum release, cpm) is obtained by adding 1% Triton X-100 to $2 \times 10^4$ target cells labeled with $^{51}$Cr at an efficiency of over 90%.

Figure 9A:
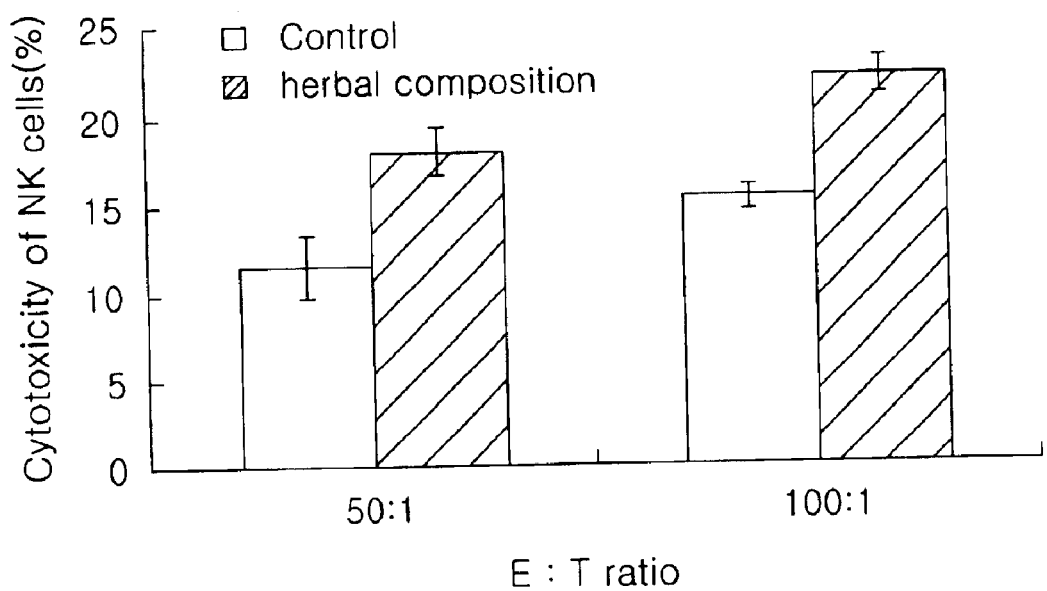
FIG. 9a is a graph showing the effects of the herbal composition of the present invention for improving the anticancer immune response of the body by activating the NK cells to increase their tumor cell-killing activity.

As shown in FIG. 9a, NK cells were found to have a 1.5 times higher cytotoxicity against the tumor cells. This result indicates that the herbal composition of the present invention activates NK cells to increase their cytotoxicity.

2.3) Effect of Improving the Anticancer Function by Activating the Macrophages

Activated macrophages play an important role in immune response systems by phagocytosis, and can also directly destroy tumor cells. The herbal composition of the present invention was evaluated for its effect on activating the macrophages to kill tumor cells. Peritoneal macrophages were isolated from abdominal cavity of the mice, aliquotted onto a 96-well flat-bottomed microplate at a density of $2 \times 10^5$ cells per well, and treated with the herbal composition of the present invention, followed by incubation for 24 hrs. After washing each well three times, the adherent macrophages were used as effector cells in the following chromium release assay to analyze their cytotoxicity against tumor cells.

$5 \times 10^3$ $^{51}$Cr-labeled YAC-1 cells as target cells were added to each well containing the cultured macrophages, in which the ratio of the effector cells to the target cells was about 40:1. After incubation for 24 hrs, 100 $\mu$l of the culture supernatant was collected into a tube, and was analyzed for the radioactive chromium released from the dead tumor cells in a gamma-counter, and the results were expressed as the average counts per minute (cpm). All the tests were carried out in triplicate, and the cytotoxicity of the macrophages against the tumor cells was calculated according to the same method as described above (Equation 1).

Figure 9B:
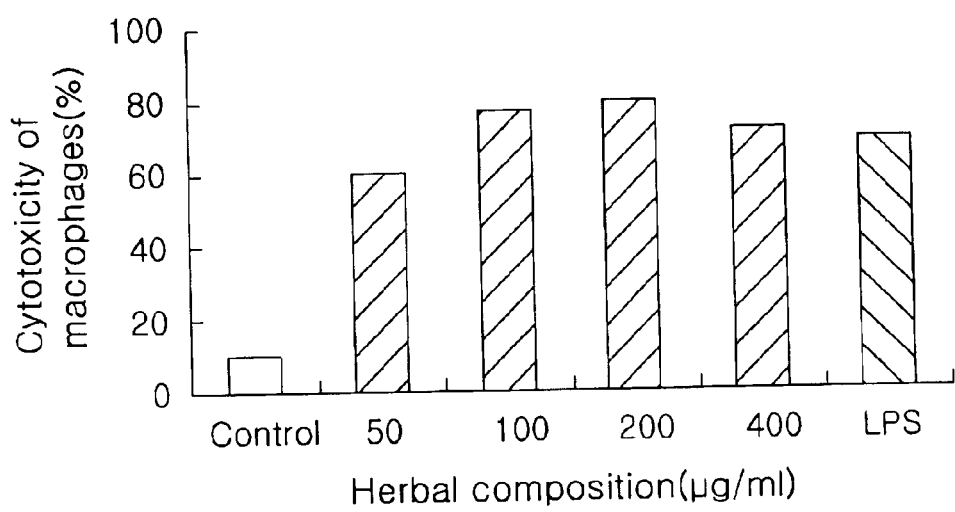
FIG. 9b is a graph showing the effects of the herbal composition of the present invention for improving the anticancer immune response of the body by activating the macrophages to increase their tumor cell-killing activity.

As shown in FIG. 9b, cytotoxicity of the macrophages against the tumor cells was found to be about 10% in a negative control, and increased to about 80% in a group treated with the herbal composition of the present invention. The increase in cytotoxicity of the macrophages treated with the herbal composition was comparable to that of the macrophages treated with a positive control chemical, LPS (lipopolysaccharide).

On the other hand, when treated with the herbal composition of the present invention, the macrophages displayed an improved phagocytosis against the added microparticles (data not shown).

2.4) Effect of Improving the Anticancer Function by Activating the Cytotoxic T Cells Destruction of tumor cells is accomplished by activation of various immune cells, and can be effectively achieved by the immune system in a specific manner. Immune cells performing such a function include cytotoxic T cells, which are able to directly kill tumor cells.

To investigate whether the herbal composition of the present invention improves the anticancer function by activating cytotoxic T cells, splenic immune cells isolated from a mouse sensitized with tumor cells were analyzed for cytotoxicity against the tumor cells. Mice were intraperitoneally administered with the herbal composition (1 mg/mouse) once daily for 3 days. Next day, mice were intraperitoneally injected with $1\times10^6$ B16F0 melanoma cells killed by being exposed to radiation. Thereafter, the herbal composition was intraperitoneally adminstered into the mice once daily for 2 more days. On day 7 after the injection with the killed tumor cells, mice were sacrificed, and the splenocytes sensitized with the tumor cells were isolated, and their cytotoxicity against tumor cells was investigated by the chromium release assay. The splenic immune cells as effector cells and $^{51}$Cr-labeled B16F0 melanoma cells were aliquotted into each well of a 96-well microplate at ratios of 50:1 and 100:1. After incubation for 4 hrs, 100 µl of the culture supernatant was collected into a tube, and was analyzed for the radioactive chromium released from the dead tumor cells in a gamma-counter, and the results were expressed as the average counts per minute (cpm). All the tests were carried out in triplicate, and the cytotoxicity of the cytotoxic T cells against the tumor cells was calculated according to the same method as described above (Equation 1).

Figure 9C:
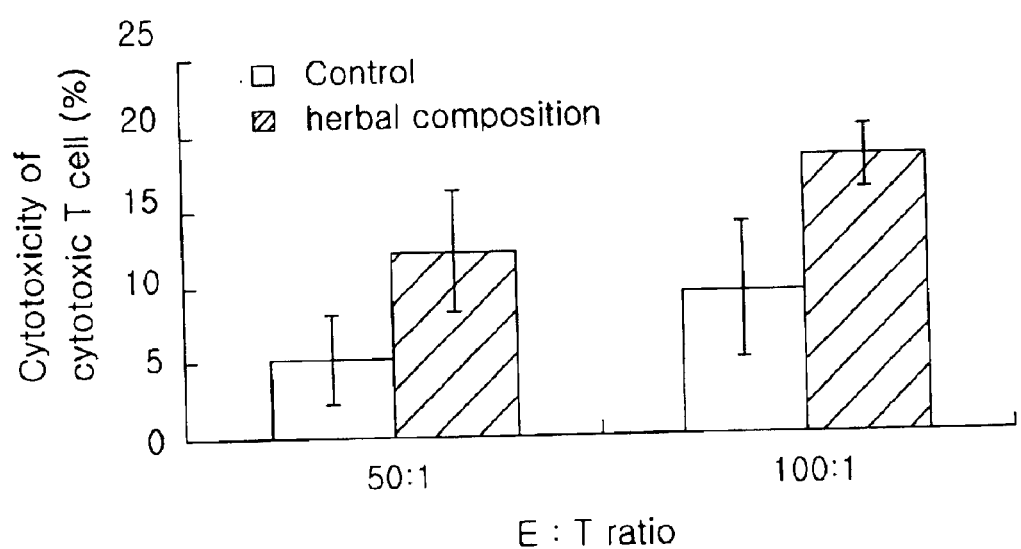
FIG. 9c is a graph showing the effects of the herbal composition of the present invention for improving anticancer immune response of the body by activating the cytotoxic T cells to increase their tumor cell-killing activity.

As shown in FIG. 9c, the herbal composition of the present invention was found to increase the cytotoxicity of the cytotoxic T cells against the tumor cells by about 2 times compared with the control.

Experimental Example 2

Evaluation of the Effect of the Herbal Composition on the Improvement of the Hematopoietic Function and the Recovery of the Hematopoietic Immune System from Oxidative Damage 1) Effect of Improving the Hematopoietic Function
1.1) Stimulation of the Proliferation of the Bone Marrow Stem Cells The herbal composition of the present invention was evaluated for the effect on the proliferation of the bone marrow stem cells. When culturing bone marrow cells, stromal cells grow adhered to the bottom of a culture dish, and non-adherent cell populations grow in suspension. The non-adherent cells proliferate via contact with the stromal cells, and differentiate into monocytes/macrophages, platelets, erythrocytes, etc. Bone marrow cells were isolated from a mouse femur. The bone marrow cells were cultured in a medium supplemented with the herbal composition and the hot-water extract prepared in Example 1. The culture supernatant containing non-adherent bone marrow stem cells was collected, and the cell number was determined using a cell counter. The results are given in FIG. 2a.

As shown in FIG. 2a, the herbal composition was found to have a stimulatory effect on the proliferation of the bone marrow stem cells, and such an effect was 1.6-fold and 7-fold higher than the effects of the hot-water extract and the control, respectively.

1.2) Stimulation of the Proliferation of the Bone Marrow Stromal Cells

It has been reported that a variety of hematopoietic factors (proteinacious factors, cytokines, etc.) secreted from the stromal cells participate in the proliferation of bone marrow stem cells and their differentiation into diverse mature cells, and contact of the bone marrow stem cells with the stromal cells near them is critical for such a proliferation and differentiation. Therefore, it is believed that the stromal cells in the hematopoietic microenvironment play an important role in regulating hematopoiesis.

Effect of the herbal composition, and the hot-water extract and its fractions on the proliferation of the bone marrow stromal cells was investigated. Bone marrow cells were cultured to obtain stromal cells adhered to the bottom of a culture dish. The isolated bone marrow stromal cells were cultured in a medium supplemented with the herbal composition and each fraction of the hot-water extract for 2–3 weeks. During the culturing, about half of a culture medium was exchanged with a fresh medium supplemented with the samples at intervals of 7 days. Proliferation of the bone marrow stromal cells was analyzed by measuring the cell numbers. The results are given in FIG. 2b.

As shown in FIG. 2b, the herbal composition of the present invention was found to have a stimulatory effect on the proliferation of the stromal cells, and such a stimulatory effect was 2-fold and 8-fold higher than that of the hot-water extract and the control, respectively.

2) Effect of Improving the Recovery of the Hematopoietic Immune System from Oxidative Damage 2.1) Effect on the Recovery of the Hematopoietic Function after Exposure to Radiation: Stimulatory Effect on the Regeneration of the Blood Cells (Immune Cells) and Splenic Immune Cells It is known that, when an animal is exposed to radiation, blood cell numbers are sharply reduced, and then recover slowly.

Before and after exposure to radiation (5 Gray), mice were administered with the herbal composition of the present invention, and the cell numbers of the blood cells and splenic lymphocytes was analyzed. 36 hrs and 12 hrs before, and 30 min and 24 hrs after exposure to radiation, the herbal composition was intraperitoneally administered into mice, and then such an administration was carried out 3 more times at intervals of 2 days.

Blood was collected from the mouse via orbital vein, and the number of blood cells was determined using an animal blood cell analyzer.

The subsets of splenic immune cells (lymphocytes; referred as 1 in FIGS. 11a and 11b) were analyzed using a flow cytometer. The prepared splenic lymphocytes were washed with phosphate-buffered saline containing 0.1% bovine serum albumin and 0.1% sodium azide, and aliquots of $10^6$ cells were transferred into test tubes. To prevent non-specific binding of the cell subset-specific antibodies to Fc γII/III receptors, the Fc receptors were blocked by incubating the lymphocytes with anti-CD16/CD32 antibody at 4° C. for 5 min. Thereafter, the lymphocytes were incubated with specific monoclonal antibodies at 4° C. for 40 min, in which anti-IgM antibody for B lymphocytes (referred as 2 in FIGS. 11a and 11b), anti-Thy1.2 antibody for all types of T lymphocytes (referred as 3 in FIGS. 11a and 11b), anti-CD4 antibody for helper T cells (referred as 4 in FIGS. 11a and 11b), and anti-CD8 antibody for cytotoxic T cells (referred as 5 in FIGS. 11a and 11b) were used. All of the antibodies were monoclonal antibodies conjugated with a fluorescent dye (FITC, fluoroisothiocyanate). Thereafter, the lymphocytes were washed twice with a phosphate-buffered saline containing 0.1% bovine serum albumin and 0.1% sodium azide, the cell numbers of each cell subset was determined by quantifying the monoclonal antibody bound to a specific cell surface marker using a flow cytometer (FACStar, COULTER, USA).

Figure 10A:
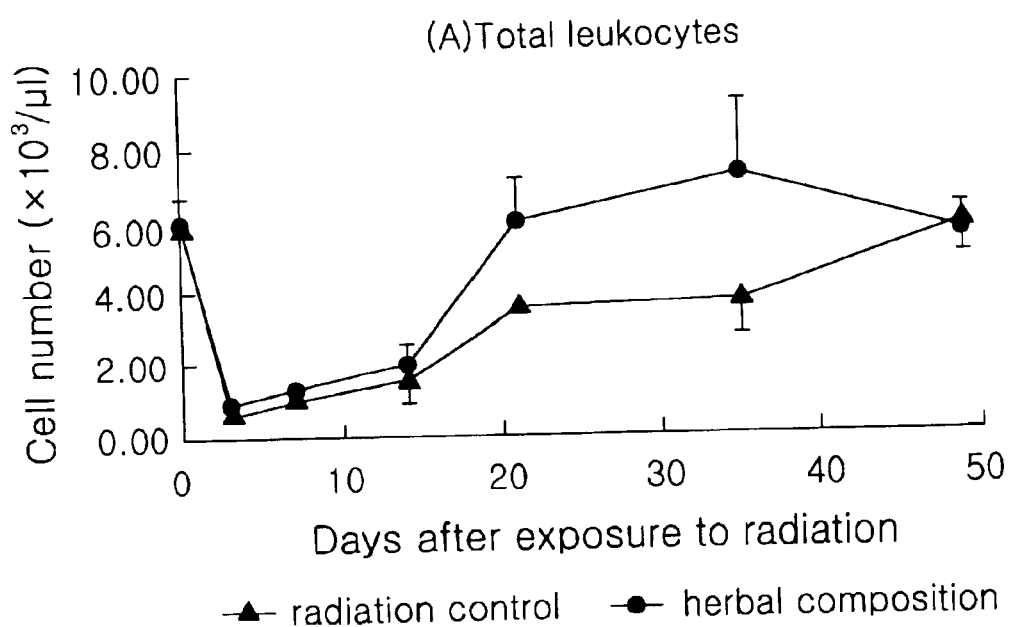
FIG. 10a is a graph showing the stimulating effect of the herbal composition of the present invention on the regeneration of leukocytes in the blood after exposure to radiation.
Figure 10B:
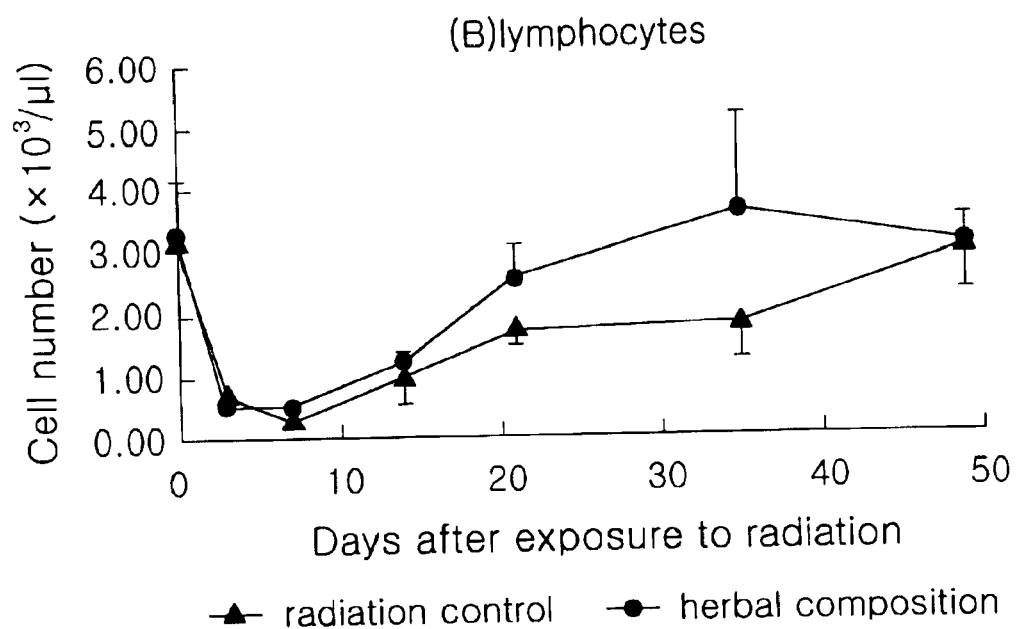
FIG. 10b is a graph showing the stimulating effects of the herbal composition of the present invention on the regeneration of lymphocytes in the blood after exposure to radiation.

As shown in FIGS. 10a and 10b, in case of the radiation-exposed mice treated with the herbal composition, from 3 weeks, the numbers of leukocytes (FIG. 10a) and lymphocytes (FIG. 10b) in the blood recovered to near the normal level, and was much higher than that of the control group exposed to radiation but not administered with the herbal composition, indicating that the herbal composition of the present invention stimulates regeneration of the leukocytes and lymphocytes in blood. In contrast, in case of the radiation-exposed control group, the numbers of leukocytes and lymphocytes recovered to a normal level after about 7 weeks.

Figure 11A:
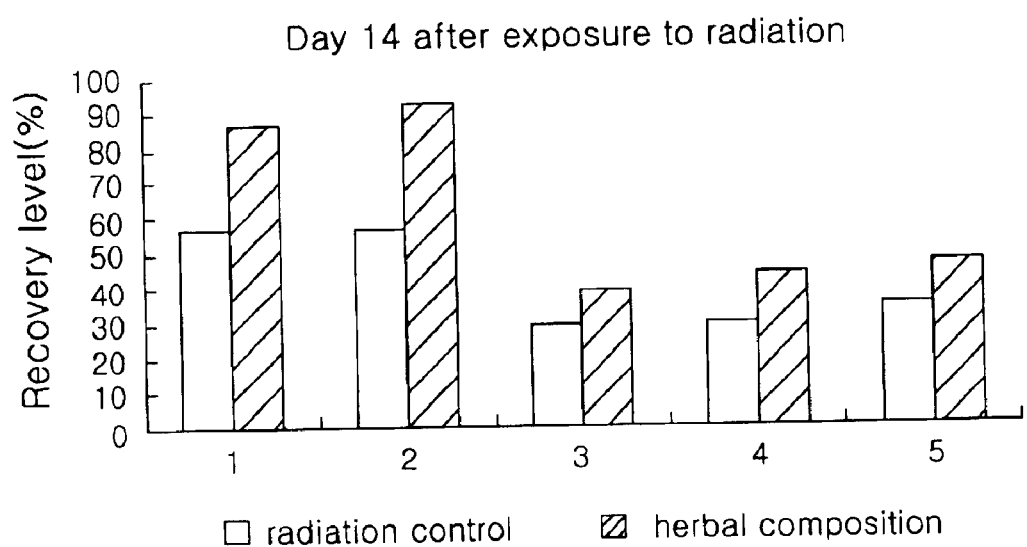
FIG. 11a is a graph showing the stimulating effects of the herbal composition of the present invention on the regeneration of each subset of the immune cells in the spleen at day 14 after exposure to radiation (1: total lymphocytes, 2: B lymphocytes, 3: T lymphocytes, 4: helper T cells, 5: cytotoxic T cells)
Figure 11B:
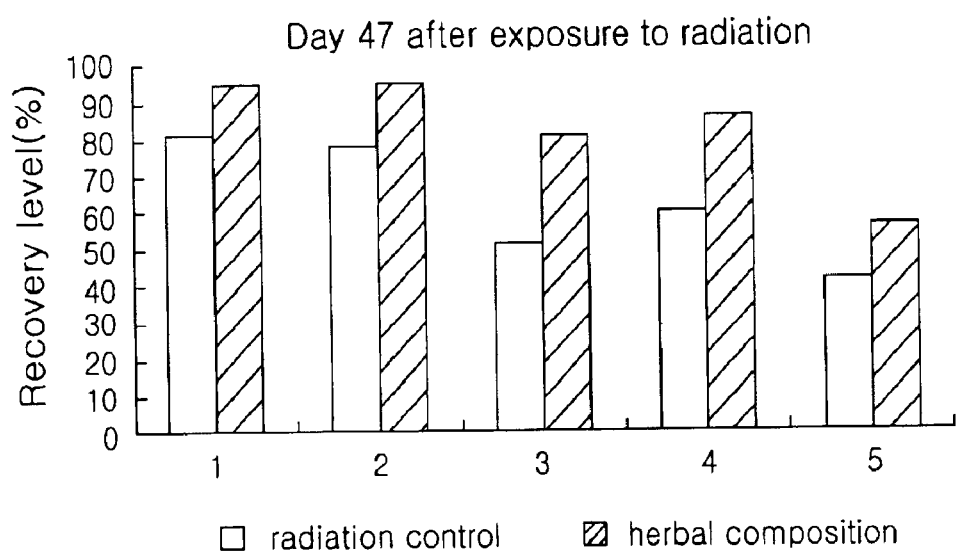
FIG. 11b is a graph showing the stimulating effect of the herbal composition of the present invention on the regeneration of each subset of the immune cells in the spleen at day 47 after exposure to radiation.

The results of the regeneration test of splenic lymphocytes are given in FIGS. 11a and 11b. As shown in FIG. 11a, on day 14 after exposure to radiation, in the case of the treatment group administered with the herbal composition, the total cell number of splenic lymphocytes was recovered to a much higher level than the radiation-exposed control group not administered with the herbal composition. With respect to the cell subsets, in the treatment group, B cells almost recovered to the normal level, while T cells and their subtypes were recovered to a higher level than the control group, but such a recovery level was no more than 50% of the normal level. Day 47 after exposure to radiation, as shown in FIG. 11b, in both the treatment and control groups, the cell numbers of the total splenic lymphocytes and B cells recovered to the normal level. Cell numbers of the T cells and their subtypes was recovered to about 50% of the normal level in the radiation-exposed control group, while almost 80% of the normal level in the treatment group.

2.2) Effect on the Recovery of the Function of the Regenerated Immune Cells after Exposure to Radiation 2.2.1) Effect of Improving the Activity of the Regenerated B Cells In order to investigate whether the herbal composition of the present invention improves the activity of the regenerated B cells in mice exposed to radiation, a plaque forming cell assay against SRBC was performed as follows.

36 hrs and 12 hrs before, and 30 min and 24 hrs after exposure to radiation (5 Gray), the herbal composition was intraperitoneally administered into mice, and then such an administration was carried out 3 more times at intervals of 2 days. Day 14 and 25 after exposure to radiation, C57BL/6 mice were injected via the tail vein with $1 \times 10^9$ sheep red blood cells (SRBC) in a 0.2 ml saline. After 4 days, splenic lymphocytes were isolated from the mice, adjusted to a density of $7 \times 10^6$ cells/ml, and placed on ice. SRBC were washed three times with a phosphate-buffered saline, and resuspened in a medium to generate a 20% (v/v) cell suspension. A 0.5% agarose-RPMI solution was prepared in a 45° C. water bath for fixing the lymphocytes and SRBC. 100 μl of the lymphocyte suspension was gently mixed with 100 μl of the SRBC suspension in 1600 μl of the 0.5% agarose-RPMI solution, and the resulting mixture was plated onto a culture dish. After hardening, the culture dish was incubated for 2 hrs in an incubator, and 600 μl of a 70-fold dilution of a Guinea pig complement (GPC) was added to the dish. After incubation for 2 more hrs, hemolytic plaques, which were formed at the surrounding of the antibody-producing cells by the interaction of the complement with the antigen(SRBC)-antibody complexes, were counted, and converted to the number of plaque forming cells (PFC) per spleen with consideration of the dilution degree of the lymphocytes. The results are given in FIGS. 12a and 12b.

Figure 12A:
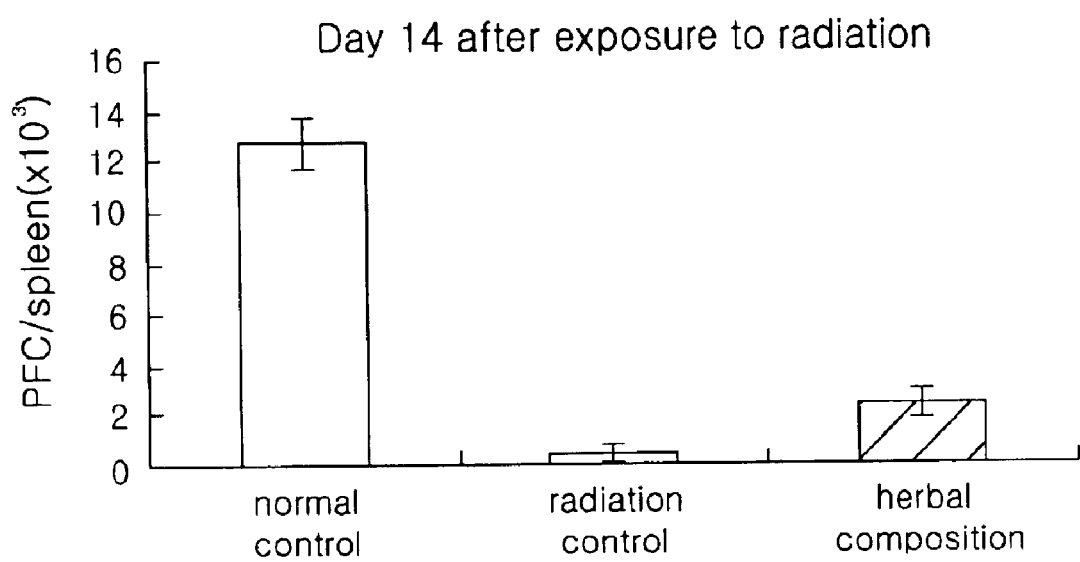
FIG. 12a is a graph showing the stimulating effects of the herbal composition of the present invention on the recovery of the function of the regenerated B cells, in the assay for the antibody-producing activity of the B cells at day 14 after exposure to radiation.
Figure 12B:
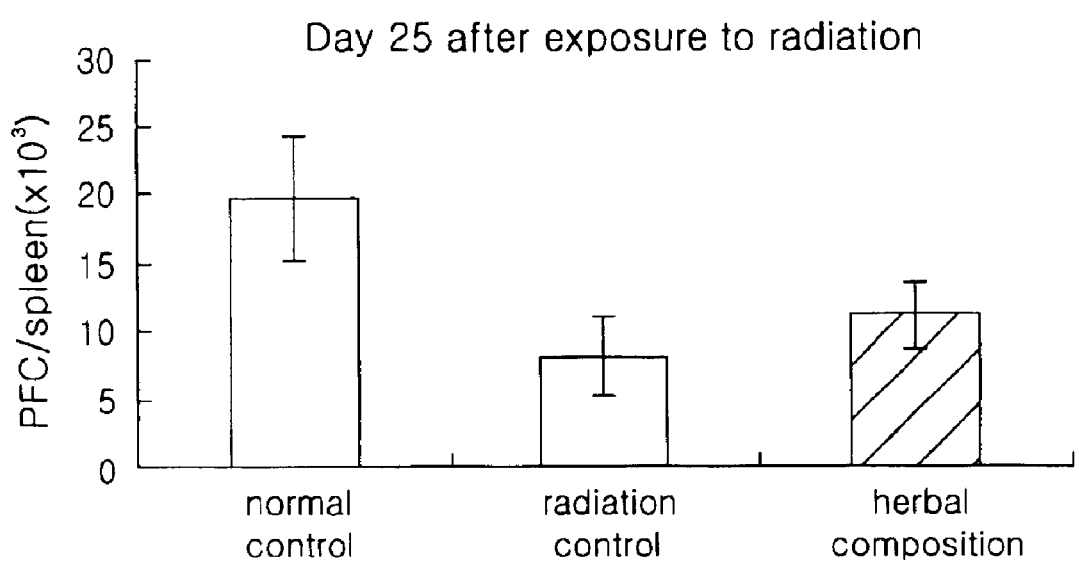
FIG. 12b is a graph showing the stimulating effects of the herbal composition of the present invention on the recovery of the function of the regenerated B cells, in the assay for the antibody-producing activity of the B cells at day 25 after exposure to radiation.

As shown in FIGS. 12a and 12b, in the case of a radiation-exposed control not treated with the herbal composition, on day 14 after exposure to radiation, although the number of B cells was recovered to about 60% of the normal level (FIG. 11a), the antibody-producing function of the B cells was only about 4% of the normal level, while being only about 41% of the normal level on day 25 after exposure to radiation. In contrast, in the case of the treatment group with the herbal composition, on days 14 and 25 after exposure to radiation, the B cells exhibited an antibody-producing function of about 20% and 57% of the normal level, respectively. These results indicate that the herbal composition of the present invention has an activity to improve the antibody-producing function of the regenerated B cells, as well as stimulating the regeneration of the B cells (FIGS. 11a and 11b).

2.2.2) Effect of Improving the Activity of the Regenerated Helper T Cells

In order to investigate whether or not the herbal composition of the present invention improves the activity of the regenerated helper T cells in mice exposed to radiation, T cell response to the stimulation of allogeneic immune cells was analyzed by the mixed lymphocyte reaction (MLR).

36 hrs and 12 hrs before, and 30 min and 24 hrs after exposure to radiation (5 Gray), C57BL/6 mice (MHC type H-2b) were intraperitoneally administered with the herbal composition, and then such an administration was carried out 3 more times at intervals of 2 days. On days 21 and 36 after exposure to radiation, mice were sacrificed, and splenic immune cells (lymphocytes) were isolated to use as responder cells. Stimulator cells were prepared by killing splenic immune cells (lymphocytes) from BALB/c(H-2d) mice by exposure to gamma-ray (3,000 rads). The responder cells and the stimulator cells were mixed and plated onto a 96-well flat-bottomed microplate at a concentration of $1 \times 10^5$ cells each in a 0.2 ml of complete medium per well, and cultured for 4 days in an incubator. 4 hrs before harvesting the cells, $^3$H-thymidine of 2 μCi was added to each well. Thereafter, cells were harvested on a glass-fiber filter paper using a cell harvester. The paper strip was put into a counting vial and a 3 ml scintillation cocktail was added to the vial. $^3$H-thymidine uptake by the responder cells was measured in a β-scintillation counter, and the results were expressed as the average counts per minute (cpm).

Figure 13A:
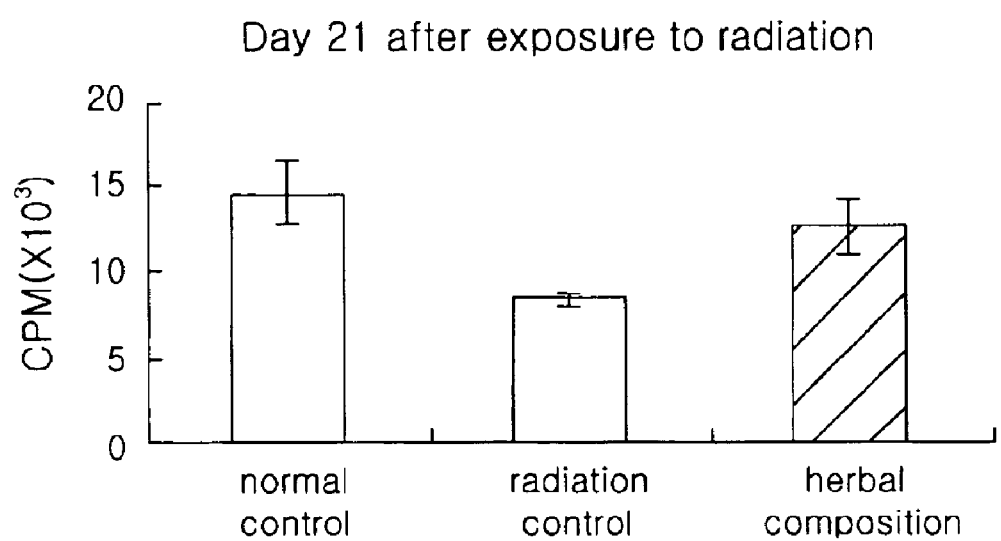
FIG. 13a is a graph showing the stimulating effects of the herbal composition of the present invention on the recovery of the function (response to allogeneic immune cells) of the regenerated T cells at day 21 after exposure to radiation.
Figure 13B:
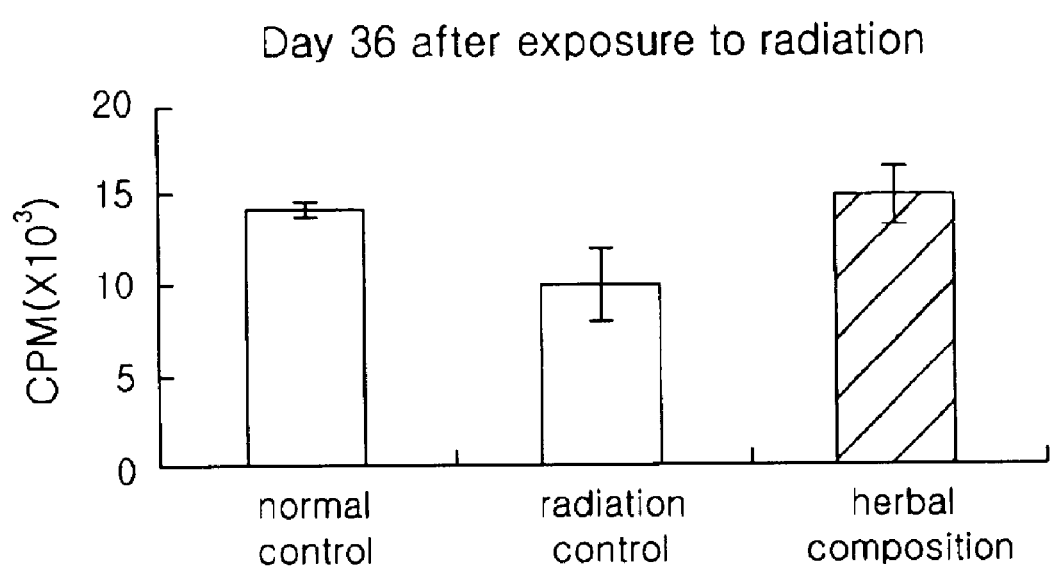
FIG. 13b is a graph showing the stimulating effects of the herbal composition of the present invention on the recovery of the function (response to allogeneic immune cells) of the regenerated T cells at day 36 after exposure to radiation.

As shown in FIGS. 13a and 13b, in the treatment group with the herbal composition of the present invention on day 21 after exposure to radiation, the response (proliferation) of the regenerated helper T cells in the MLR assay was found to be much higher than the radiation-exposed control not treated with the herbal composition. About 5 weeks after exposure to radiation, in the treatment group, the response (proliferation) of the regenerated helper T cells had recovered to the normal level. These results indicate that the herbal composition of the present invention has an activity to improve the response of the regenerated helper T cells.

2.2.3) Effect of Normalizing the Disturbed Pattern of Antibody Production after Exposure to Radiation In order to investigate whether or not the herbal composition of the present invention regulates the disturbed antibody production pattern in radiation-exposed mice, the production level of each antibody type was measured after injection with a T cell-dependent antigen.

36 hrs and 12 hrs before, and 30 min and 24 hrs after exposure to radiation, mice were intraperitoneally administered with the herbal composition, and then such an administration was carried out 3 more times at intervals of 2 days. On week 1, 2, 3, 5 and 8 after exposure to radiation, mice were intraperitoneally injected with a protein antigen (DNP-KLH). On day 7 and 14 after the antigen injection, blood was collected from the mice via orbital vein, and serum was isolated and stored at −70° C. until use. The stored serum was analyzed for antibody titer by enzyme-linked immunosorbent assay (ELISA), as follows. After coating each well of a microplate with the antigen, the serum was added to the well to allow the antibody in the serum to interact with the coated antigen. After washing the well, peroxidase-conjugated goat anti-mouse IgG or biotin-conjugated anti-mouse IgE was added to the well to interact with antigen-bound antibody. In the case of the addition of the biotin-conjugated IgE, streptavidin-conjugated horse peroxidase was added to the well to interact further with the conjugated biotin. A TMB substrate of the peroxidase was added for colour development. After stopping the colour development, absorbance was measured at 450 nm using an ELISA reader, in which a reference wavelength was 570 nm.

Figure 14A:
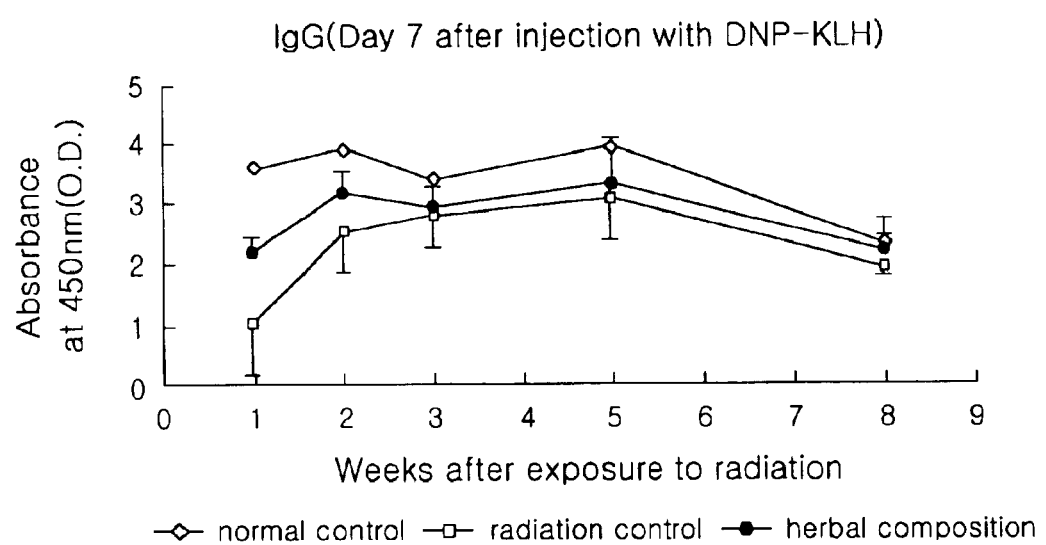
FIG. 14a is a graph showing the regulating effects of the herbal composition of the present invention on the disturbed pattern of antibody production by recovering the reduced production of IgG after exposure to radiation.
Figure 14B:
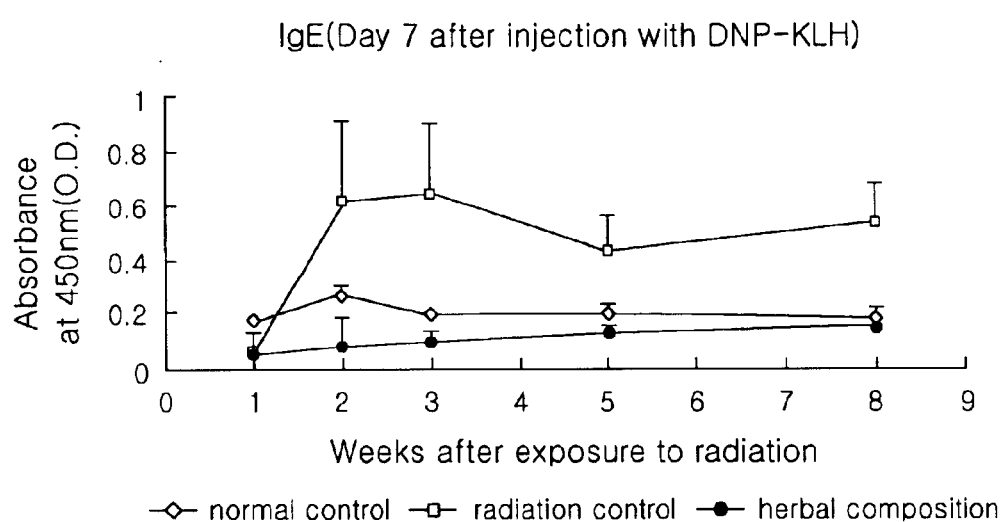
FIG. 14b is a graph showing the regulating effects of the herbal composition of the present invention on the disturbed pattern of antibody production by lowering the overproduction of IgE after exposure to radiation.

As shown in FIGS. 14a and 14b, when exposed to radiation, mice exhibited reduced IgG production in comparison with the normal control (FIG. 14a), while displaying an increased IgE production (FIG. 14b). Such a change in IgG and IgE production by irradiation was almost recovered to the normal pattern by the administration with the herbal composition of the present invention.

2.2.4) Effect of Improving the Cytotoxicity of the Regenerated NK Cells Against the Tumor Cells In order to investigate whether or not the herbal composition of the present invention improves the activity of the regenerated NK cells in radiation-exposed mice, the splenic lymphocytes isolated from the mice were evaluated for cytotoxicity against tumor cells by the chromium release assay (see, 2.2).

36 hrs and 12 hrs before, and 30 min and 24 hrs after exposure to radiation (5 Gray), mice were intraperitoneally administered with the herbal composition. On days 22, 29, 35 and 49 after exposure to radiation, splenocytes were isolated from the mice, and lymphocytes were obtained from the splenocytes by Ficoll-Hypaque density gradient centrifugation. The lympocytes were resuspended in a complete medium to use as effector cells in the following chromium release assay, in which YAC-1 cells ($2\times10^5$ cells/ml) labeled with $^{51}$Cr were used as target cells. Both the effector cells and the target cells, at 0.1 ml each, were plated onto a 96 well-round bottomed microplates at ratios of 6.5:1, 12.5:1, 25:1 and 50:1. After incubation for 4 hrs, 0.1 ml of the culture supernatant was collected, and the amount of radioactive chromium was measured in a gamma-counter. All the tests were carried out in triplicate, and the cytotoxicity of the lymphocytes against the tumor cells was calculated according to the same method as described above (Equation 1).

To compare tumor cell-killing activity of the splenic lymphocytes in individual mice, the number of lymphocytes (lytic unit: LU) required for killing a desired number of tumor cells was calculated. In this test, 1 $LU_{10}$ was defined as the number of effector cells necessary for 10% lysis of the target cells. $LU_{10}$ was calculated from a dose response curve by linear regression analysis. Tumor cell-killing activities between individual mice were compared by calculating the LU per spleen by multiplying LU per $1\times10^7$ lymphocytes by the total number of splenic lymphocytes.

Figure 15:
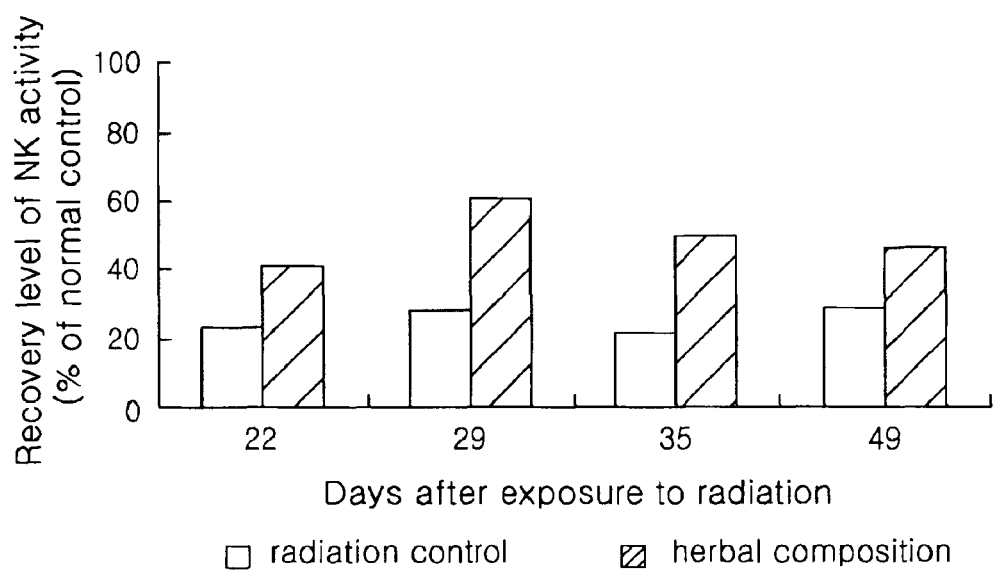
FIG. 15 is a graph showing the stimulating effects of the herbal composition of the present invention on the recovery of the tumor cell-killing activity of the regenerated NK cells after exposure to radiation.

As shown in FIG. 15, in the case of the control exposed to radiation, the regenerated NK cells exhibited remarkably diminished tumor cell-killing activity for a long period of time after exposure to radiation. In contrast, in the case of the treatment group administered with the herbal composition, the function (tumor cell-killing activity) of the regenerated NK cells was remarkably recovered to about a 2-fold higher level than the radiation-exposed control.

Experimental Example 3

Evaluation of the Effect of the Herbal Composition on the Protection of the DNA and Chromosomes from Oxidative Damage 1) Inhibitory Effect Against Oxidative Damage of the Intracellular DNA and Chromosomes After treating lymphocytes with the herbal composition, and the hot-water extract and its isolated fractions for 4 hrs, and then exposing them to radiation or treatment with $H_2O_2$, the damage of the intracellular DNA and chromosomes was compared with that of the control exposed to radiation.

1.1) Inhibitory Effect Against Oxidative DNA Damage

In order to investigate whether or not the herbal composition of the present invention prevents single-strand DNA breakage resulting from oxidative damage induced by radiation or chemical compounds, a single-cell gel electrophoresis assay (comet assay) was performed as follows.

First, the treated cells were mixed with agarose gel and spread on a microscope slide. The cells were then lysed in a lysis buffer at 4° C. for 1 hr. The slide was subjected to electrophoresis, and the DNA fragments were stained with ethidium bromide (20 μg/ml). The migrated DNA fragments were analyzed by an image analysis system (Komet 4.0, Kinetic imaging, Ltd., Great Britain) under a fluorescent microscope equipped with a CCD camera. Extent of DNA damage was expressed as the tail moment (TM), where TM=migration length of the DNA fragments (tail length)× the percentage of DNA fragments in the tail. A higher tail moment means higher DNA damage.

As a result, the herbal composition of the present invention was found to effectively inhibit single-strand DNA breakage induced by radiation (FIG. 3a) and $H_2O_2$ (FIG. 3b), in which the inhibition rate was about 49% and 37%, respectively.

1.2) Inhibitory Effect Against Oxidative Chromosome Damage

In order to investigate whether or not the herbal composition of the present invention prevents chromosome aberration caused by oxidative damage by radiation and chemical compounds, the frequency of the micronucleus formed during the nuclear division of the cells with chromosome damage was measured in a micronucleus test.

First, lymphocytes were cultured in a medium added with the herbal composition of the present invention for 4 hrs, and then exposed to radiation or treated with $H_2O_2$. The cells were treated with cytochalasin B to prevent the division of the cytoplasmic membrane. After 24 hrs, the cells were collected, placed onto a microscope slide, and Giemsastained. Micronucleus frequency was scored in 1,000 binucleated cells that had undergone nuclear division.

As a result, the herbal composition was found to effectively inhibit chromosome aberration caused by oxidative damage by radiation (FIG. 4a) and $H_2O_2$ (FIG. 4b), in which the inhibition rate was about 33% and 64%, respectively.

2) Inhibition of the Oxidation of the Intracellular Lipids and Proteins 2.1) Inhibition of Lipid Peroxidation In order to investigate whether or not the herbal composition of the present invention inhibits peroxidation of membrane lipids induced by radiation and chemical compounds, malondialdehyde produced by lipid peroxidation in mouse liver was measured in the thiobarbituric acid reactive substance (TBARS) assay.

36 hrs and 12 hrs before exposure to radiation (8 Gray), mice were intraperitoneally administered with the herbal composition and each fraction of the hot-water extract.

To induce oxidative damage by a chemical compound, mice were intraperitoneally injected with a mixture (0.5 ml/kg) of $CCl_4$ and corn oil, and starved for about 18 hrs to induce liver damage. In this case, the herbal composition and each fraction of the hot-water extract were intraperitoneally injected into mice 27 hrs and 3 hrs before treatment with $CCl_4$.

After sacrificing the mice, the livers were excised, and homogenized. The homogenized liver samples containing 3 mg of protein were mixed with 0.2 ml of 8.1% SDS (sodium dodecyl sulfate), 1.5 ml of 20% acetic acid and 1.5 ml of 0.8% TBA solution, and the mixture was incubated at 95° C. for 30 min in a water bath. Absorbance was measured at 532 nm. On a standard curve obtained using a standard solution of 1,1,3,3-tetraethoxypropane, the amount of the produced malondialdehyde was estimated and expressed as nmol/mg protein.

As a result, the herbal composition of the present invention was found to effectively inhibit lipid peroxidation induced by radiation (FIG. 5a) and $CCl_4$ (FIG. 5b), in which the inhibition rate was about 31% and 36%, respectively.

2.2) Inhibition of Protein Oxidation

In order to investigate whether or not the herbal composition of the present invention inhibits protein oxidation by radiation, carbonyl groups in mouse liver proteins were quantified, in which the carbonyl groups are formed in some amino acid residues of the proteins by oxidation thereof.

36 hrs and 12 hrs before exposure to radiation (8 Gray), mice were intraperitoneally administered with the herbal composition and each fraction of the hot-water extract. 4 hours after exposure to radiation, mouse livers were excised, and homogenized. Homogenized liver samples containing 4 mg of protein were mixed with an equal volume of 20% TCA (trichloroacetic acid) to precipitate the proteins. The precipitated protein sample was reacted with 500 µl of 10 mM 2,4-dinitrophenylhydrazine (DNPH) for 1 hr, and an equal volume of 20% TCA was added, followed by centrifugation. After discarding the supernatant, the protein pellet was washed with 1 ml of ethanol/ethyl acetate (1:1), and resuspended with 1.2 ml of 6M guanidine.HCl, followed by centrifugation. The absorbance of the supernatant was measured spectrophotometrically at 370 nm. The concentration of carbonyl groups was calculated from the absorbance, using a molar absorption coefficient of 22,000 $mol/L^{-1}$ $cm^{-1}$.

As a result, the herbal composition of the present invention was found to remarkably inhibit the protein oxidation induced by radiation, so the protein oxidation was similar to that of the normal control (FIG. 5c).

3) Effect of Scavenging Free Radicals 3.1) Effect of Scavenging DPPH Radical

In order to investigate whether or not the herbal composition of the present invention has a radical scavenging activity by donating electrons to free radical molecules generated in the body, the electron-donating ability of the herbal composition to the DPPH (1,1-diphenyl-2-picrylhydrazyl) radical was measured.

1.8 ml of $4\times10^{-4}$ M DPPH was added to 0.2 ml of the herbal composition, and the hot-water extract and its fractions at various concentrations, and the mixture was well mixed with a vortex for 10 sec. After incubation for 30 min, absorbance was measured at 517 nm using a spectrophotometer (Shimadzu UV-1201, Japan). The DPPH radical has a deep violet color due to its unpaired electron. When the test sample donates electrons to the DPPH radical, that is, the unpaired radical electron is stabilized by pairing with the donated electron, the color turns from deep violet into pale yellow and the absorbance at 517 nm decreases. Using this principle, the electron-donating ability (EDA) of the test samples was expressed as the percentage of the difference in absorbance at 517 nm between the test solution and the control solution.

$$EDA(\%)=(Ac-As)/Ac\times100$$

wherein, Ac is the absorbance of the control solution not containing the test sample, and As is absorbance of the test solution containing the test sample.

As a result, the hot-water extract, and its ethanol and methanol fractions showed a very high electron-donating activity, and the polysaccharide fraction and the herbal composition exhibited a significant electron-donating activity (FIG. 6a).

3.2) Effect of Scavenging OH Radical

In order to investigate whether or not the herbal composition of the present invention has an activity to scavenge OH (hydroxyl) radicals mostly responsible for in vivo oxidative damage, which has a relatively strong reactivity among the reactive oxygen species, the herbal composition was evaluated for OH radical-scavenging activity, in which the OH radical was produced in vitro using $H_2O_2$ (2-deoxyribose oxidation method).

0.2 ml of each sample of the herbal composition, and the hot-water extract and its fractions was mixed with 0.2 ml of 0.1 mM $FeSO_4$/EDTA, 0.2 ml of 10 mM 2-deoxyribose, and 1.2 ml of 0.1 M phosphate buffer (pH 7.4). Then, 0.2 ml of 10 mM $H_2O_2$ was added to the mixture. After incubation at 37° C. for 4 hrs, reaction was stopped by the addition of 1 ml of 2.8% TCA (trichloroacetic acid). After the addition of 1 ml of 1% TBA (2-thiobarbituric acid), the final reaction mixture was incubated at 95° C. for 10 min in a water bath, and cooled. Absorbance at 532 nm was measured in an UV-spectrophotometer. Hydroxyl radical scavenging activity was expressed as the percentage of the difference in absorbance at 532 nm between the test solution and the control solution.

$$\text{Hydroxyl radical scavenging activity }(\%)=[1-(As-Ao)/(Ac-Ao)]\times100$$

wherein, Ao is the absorbance of the negative control not containing both the test sample and $H_2O_2$, Ac is the absorbance of the positive control treated with $H_2O_2$ but not containing the test sample, and As is the absorbance of the test solution containing the test sample and treated with $H_2O_2$.

The results are given in FIG. 6b. The herbal composition of the present invention was found to have the highest OH radical-scavenging activity.

Experimental Example 4

Toxicity Test

As a result of a toxicity test in which the herbal composition of the present invention was administered orally and intraperitoneally into mice, a 50% lethal dose (LD50) was found to be over 2 g per kg body weight, indicating that the herbal composition has no toxicity.

Effect of the Invention

As described hereinbefore, the herbal composition of the present invention has an effect of improving the anticancer activity, immune function and hematopoietic function of the body, and inhibiting oxidative damage to the body. Therefore, the herbal composition can be applied for the prevention of side effects of cancer therapy by stimulating the recovery of the damaged immune function and hematopoietic function, and inhibiting oxidative damage. Further, owing to its advantageous properties, the herbal composition can be applied for preventing various degenerative chronic diseases and improving the health of the weak and the elderly.

What is claimed is:

1. An herbal composition for improving anticancer activity, immune response and hematopoiesis of the body, and protecting the body from oxidative damage, comprising an effective amount of a first hot-water extract from a mixture of the plants *Angelicae gigantis* Radix, *Cnidium officinale* Makino and *Paeonia japonica* Miyabe et Takeda at an equal weight ratio, and an effective amount of a polysaccharide fraction as a precipitate formed by adding ethanol to a second hot-water extract from a mixture of the plants *Angelicae gigantis* Radix, *Cnidium officinale* Makino and *Paeonia japonica* Miyabe et Takeda at an equal weight ratio.

2. The herbal composition as set forth in claim 1, wherein the amount of the second hot-water extract is 0.5 to 3 times the amount of the first hot-water extract.

3. A pharmaceutical composition for treating cancer, comprising the herbal composition of claim 1 as an effective ingredient.

4. A pharmaceutical composition for improving the immune function, comprising the herbal composition of claim 1 as an effective ingredient.

5. A pharmaceutical composition for improving the hematopoietic function, comprising the herbal composition of claim 1 as an effective ingredient.

6. A pharmaceutical composition for protecting the body from oxidative damage, comprising the herbal composition of claim 1 as an effective ingredient.

7. A pharmaceutical composition for preventing the side effects of cancer therapy, comprising the herbal composition of claim 1 as an effective ingredient.

8. A functional food for treating cancer, improving the immune function and hematopoietic function, protecting the body from oxidative damage, and preventing the side effects of cancer therapy, comprising the herbal composition of claim 1 as an effective ingredient.

9. A method of preparing an herbal composition, comprising the following steps:
 (1) preparing a mixture consisting of the plants *Angelicae gigantis* Radix, *Cnidium officinale* Makino and *Paeonia japonica* Miyabe et Takeda at an equal weight ratio, adding water at 5 to 20 times the total weight of the mixture, and heating the resulting mixture to prepare a first hot-water extract; and
 (2) adding ethanol to a second hot-water extract prepared according to the same method as in Step (1), and collecting the precipitate to obtain a polysaccharide fraction; and
 (3) mixing an effective amount of the polysaccharide fraction prepared in Step (2) with an effective amount of the hot-water extract prepared in Step (1) to generate a herbal composition.

10. The method as set forth in claim 9, wherein, in Step (2), the second hot-water extract is used at 0.5 to 3 times the amount of the first hot-water extract prepared in Step (1).

* * * * *